US010451536B2

(12) United States Patent
Thomas

(10) Patent No.: US 10,451,536 B2
(45) Date of Patent: Oct. 22, 2019

(54) METHOD AND APPARATUS FOR MULTI-PARAMETER DATA ANALYSIS

(75) Inventor: Nicholas Thomas, Cardiff (GB)

(73) Assignee: GE HEALTHCARE UK LIMITED, Little Chalfont (GB)

( * ) Notice: Subject to any disclaimer, the term of this patent is extended or adjusted under 35 U.S.C. 154(b) by 1247 days.

(21) Appl. No.: 13/265,439

(22) PCT Filed: Apr. 23, 2010

(86) PCT No.: PCT/EP2010/055439
§ 371 (c)(1),
(2), (4) Date: Oct. 20, 2011

(87) PCT Pub. No.: WO2010/122147
PCT Pub. Date: Oct. 28, 2010

(65) Prior Publication Data
US 2012/0035859 A1 Feb. 9, 2012

(30) Foreign Application Priority Data

Apr. 24, 2009 (GB) .................................. 0907079.8

(51) Int. Cl.
*G06F 19/22* (2011.01)
*G01N 15/14* (2006.01)

(52) U.S. Cl.
CPC ..... *G01N 15/1429* (2013.01); *G01N 15/1475* (2013.01); *G01N 2015/1477* (2013.01); *G01N 2015/1497* (2013.01)

(58) Field of Classification Search
CPC .... G06F 19/24; G06F 19/18; G06F 17/30539; G06F 19/12; G06F 19/22; G06F 19/20; G06F 19/28; G06F 17/30327; G06F 17/3053; G06F 17/30598; G06F 19/34; G06F 19/706; G06F 19/707; G06F 16/24578; G06F 17/15; G06F 17/16; G06F 17/16; G06K 9/6269; G06K 9/6224; G06K 9/0014; G06K 9/00147; G06K 9/00127; G06K 9/00134; G06K 9/6253; G06K 9/00; G06K 9/34; G06K 9/4609; G06K 9/6228; G06N 5/02; G06N 99/005; G06T 2207/10056; G06T 1/60; G06T 2200/28; G06T 2207/30024; G06T 5/009; G06T 7/0012; G06T 7/602; G06T 2207/10064; G06T 2207/20152; G06T 7/12; G06T 2207/20064; G06T 2207/20081; G06T 7/0014; G06T 7/62; G06T 2200/24; G06T 2207/10024; G06T 2207/20016; G06T 2207/20036; G06T 2207/20044; G06T 2207/20072; G06T 2207/20076; G06T 2207/20084; G06T 2207/20092; G06T 5/50; G06T 7/11; G06T 7/136; G06T 7/155; G06T 7/187; G06T 7/42; G06T 7/44; G06T 7/66;
G06T 7/90; G06T 2207/20056; G16C 20/00; G16C 20/30; G16C 20/40; G16C 99/00; G02B 21/0028; C12Q 2600/106; C12Q 2600/158; C12Q 1/6886; C12Q 2600/156; C12Q 1/6883; C12Q 1/68; C12Q 1/6827; C12Q 1/6881; C12Q 2537/159; C12Q 1/00; C12Q 1/025; C12Q 2600/112; C12Q 2600/118; G01N 33/57484; G01N 2500/10; G01N 2333/47; G01N 2800/50; G01N 33/502; G01N 33/5026; G01N 33/574; G01N 1/30; G01N 2015/1006; G01N 33/4833; G01N 33/5035; G01N 33/56966; G01N 15/1475; G01N 1/36; G01N 2015/0065; G01N 2015/1402; G01N 2015/1477; G01N 2021/6439; G01N 21/00; G01N 21/6428; G01N 33/5008;

(Continued)

(56) References Cited

U.S. PATENT DOCUMENTS 8,041,090 B2 * 10/2011 Alexandrov et al. ......... 382/128
9,213,030 B2 * 12/2015 Wenk ............... G01N 33/57449

(Continued)

FOREIGN PATENT DOCUMENTS

| JP | 2007-526454 A | | 9/2007 |
| JP | 2008-507995 A | | 3/2008 |
| WO | WO2007028944 | * | 1/2007 |
| WO | 2008/018905 A2 | | 2/2008 |
| WO | 2008/089397 A2 | | 7/2008 |

OTHER PUBLICATIONS

Johnston, High Content Screening: Science Techniques and Applications, (ed S A Harvey) John Wiley and Sons Inc, Hoboken NJ, USA 2008, published online Jun. 27, 2007.*

(Continued)

*Primary Examiner* — Mary K Zeman
(74) *Attorney, Agent, or Firm* — Hanley, Flight and Zimmerman, LLC

(57) ABSTRACT

In one aspect, the present invention relates to a method 200 for identifying one or more phenotypes from a multi-parameter data set. The method 200 comprises measuring 202 correlation between pairs of parameters within the multi-parameter data set, modifying 204 correlated parameter values within a predetermined multi-parameter data analysis set to form an analysis parameter set, and analyzing 206 the multi-parameter data set using the analysis parameter set to identify one or more phenotypes from the multi-parameter data set. Various embodiments of the present invention may, for example, be used in an automated high-content screening (HCS) apparatus 100 for biological cellular analysis.

24 Claims, 15 Drawing Sheets

(58) Field of Classification Search
CPC .............. G01N 33/505; G01N 33/5061; G01N 33/5067; G01N 33/507; G01N 33/5073; G16B 40/00; G16B 25/10; G16B 5/00; G16B 20/00; G16B 25/00; G16B 30/00; G16B 40/30; G16B 50/00; G16H 50/20; G16H 50/70; G16H 10/40; G16H 50/30; A61B 5/0075; C40B 30/06

See application file for complete search history.

(56) References Cited

U.S. PATENT DOCUMENTS

| | | |
|---|---|---|
| 2005/0246105 A1 | 11/2005 | Faber et al. |
| 2006/0154236 A1* | 7/2006 | Altschuler et al. ............. 435/4 |
| 2008/0138820 A1* | 6/2008 | Thomas ........................ 435/6 |
| 2009/0075833 A1 | 3/2009 | Chinnaiyan et al. |
| 2009/0131270 A1 | 5/2009 | Taylor et al. |
| 2009/0170091 A1 | 7/2009 | Giuliano et al. |

OTHER PUBLICATIONS

Tao, C.Y. et al. Journal of Biomolecular Screening, 12 (4) 2007.*
Low, J. Current opinion in drug discovery and development 2008 11(3) 338-345.*
Perlman, Z., et al., Science, 306, 1194-1198 (2004).
Oliver Durr, Robust Hit Identification by Quality Assurance and Multivariate Data Analysis of a High-Content, Cell Based Assay, J. Biomol Screen, 2007, vol. 12, No. 8, pp. 1042-1049.
Nathalie Malo, Statistical practice in high-throughput screening data analysis, Nature Biotechnology, Feb. 2006, vol. 24, No. 2, pp. 167-175.

* cited by examiner

METHOD AND APPARATUS FOR MULTI-PARAMETER DATA ANALYSIS

CROSS-REFERENCE TO RELATED APPLICATIONS

This application is a filing under 35 U.S.C. § 371 and claims priority to international patent application number PCT/EP2010/055439 filed Apr. 23, 2010, published on Oct. 28, 2010 as WO 2010/122147, which claims priority to application number 0907079.8 filed in Great Britain on Apr. 24, 2009.

FIELD OF THE INVENTION

The present invention relates generally to a method and apparatus for analysis of multi-parameter data. More specifically, the present invention relates to the analysis of multi-parameter data in order to identify one or more phenotypes. Using such phenotypes, various embodiments of the present invention may, for example, be used in automated high-content screening (HCS) that uses biological cellular image analysis.

BACKGROUND OF THE INVENTION

HCS, the application of automated sub-cellular imaging and image analysis to investigating cellular signalling pathways and processes (S. A. Haney, P. LaPan, J. Pan and J. Zhang, "High-content screening moves to the front of the line," Drug Discovery Today, Vol. 11, No. 19-20, pp. 889-894, October 2006), is becoming widely adopted across both industry and academia as a rapid and cost-effective route to generating highly informative biological data. HCS provides investigators with powerful technologies and applications for detailed investigation of cellular biology in-situ and in-context, and as a consequence generates large multi-parameter data sets corresponding, for example, to various respective images.

In many studies the full potential of this data has not been fully explored or exploited. Standard methods of data analysis and comparison, such as the use of mean and standard deviation, which have been routinely used in high-throughput screening (HTS), obscure underlying patterns and trends in HCS data by averaging cellular population responses.

A simple example of this obscuration occurs in chemical inhibitor or RNAi studies, where, for example, a 50% decrease measured by HTS metrics as a mean response may represent 50% inhibition in all cells or, alternatively, 100% inhibition in 50% of cells, with the remainder being unaffected.

The situation is further worsened by the typical distributions of cellular intensity or spatial data, which is rarely, if ever, normally distributed, thus making mean and standard deviation a poor descriptor of the data distribution.

Consequently comparison of HCS data between samples based on averaged responses is not only underutilising the data but is also likely to be inaccurate in many cases.

Limitations of standard data averaging techniques have led to the adoption of various non-parametric analysis methods, such as use of the Kolmogorov-Smirnov (KS) distance (S. Siegel and N. J. Castellan, Non-Parametric Statistics for the Behavioural Sciences, McGraw-Hill, New York, USA, $2^{nd}$ Edition, 1988) for comparing cell population data and distributions in HCS data (Z. E. Perlman, M. D. Slack, Y. Feng, T. J. Mitchison, L. F. Wu and S. J. Altschuler, "Multidimensional drug profiling by automated microscopy," Science, Vol. 306, pp. 1194-1198, 12 Nov. 2004; and B. Zhang, X. Gu, U. Uppalapati, M. A. Ashwell, D. S. Leggett and C. J. Li, "High-content fluorescent-based assay for screening activators of DNA damage checkpoint pathways," Journal of Biomolecular Screening, Vol. 13, No. 6, pp. 538-543, 19 Jun. 2008).

For example, US 2006/0154236 (Altschuler et al) describe methods and systems for the analysis of cells based on the automated collection of data from image processing software and statistical analysis of this data. The methods described include the use of intra-sample KS distance as a measure of population differences and means for normalising KS distance by dividing by a measure of the variability of the descriptor (e.g. standard deviation) within a population.

However, whilst the use of such non-parametric data analysis methods is an improvement on previous techniques, there still remains the need for both faster and more accurate data analysis techniques, particularly for analysing the extremely large multi-parameter data sets typically generated by HCS/HTS.

SUMMARY OF THE INVENTION

The present invention has thus been devised whilst bearing the above-mentioned drawbacks associated with conventional data analysis methods in mind.

According to a first aspect of the present invention, there is provided a method for identifying one or more phenotypes from a multi-parameter data set. The method comprises measuring correlation between pairs of parameters within the multi-parameter data set, modifying correlated parameter values within a predetermined multi-parameter data analysis set to form an analysis parameter set, and analysing the multi-parameter data set using the analysis parameter set to identify one or more phenotypes from the multi-parameter data set.

According to a second aspect of the present invention, there is provided an apparatus for automated high-content screening (HCS) of one or more multi-parameter data sets. The apparatus comprises a processor that is operable to measure correlation between pairs of parameters within a multi-parameter data set. The processor is also operable to modify correlated parameter values within a predetermined multi-parameter data analysis set for the multi-parameter data set to form an analysis parameter set and to analyse the multi-parameter data set using the analysis parameter set to identify one or more phenotypes from the multi-parameter data set.

Modification of correlated parameter values within a predetermined multi-parameter data analysis set may comprise multiplication or other arithmetic modification of the parameter values using one or more factors derived from correlation measurements, including modification of the parameter value to zero, or removal of the parameter from further analysis, for example.

By determining phenotypes from an analysis parameter set that is formed of independent, or substantially non-correlated, parameters overall data processing time is reduced.

Moreover, this technique additionally provides for more accurate measurement of phenotypes thereby enabling improved feature recognition to be provided automatically at high speed, for example, in a HCS/HTS system.

DETAILED DESCRIPTION OF THE INVENTION

Figure 1:
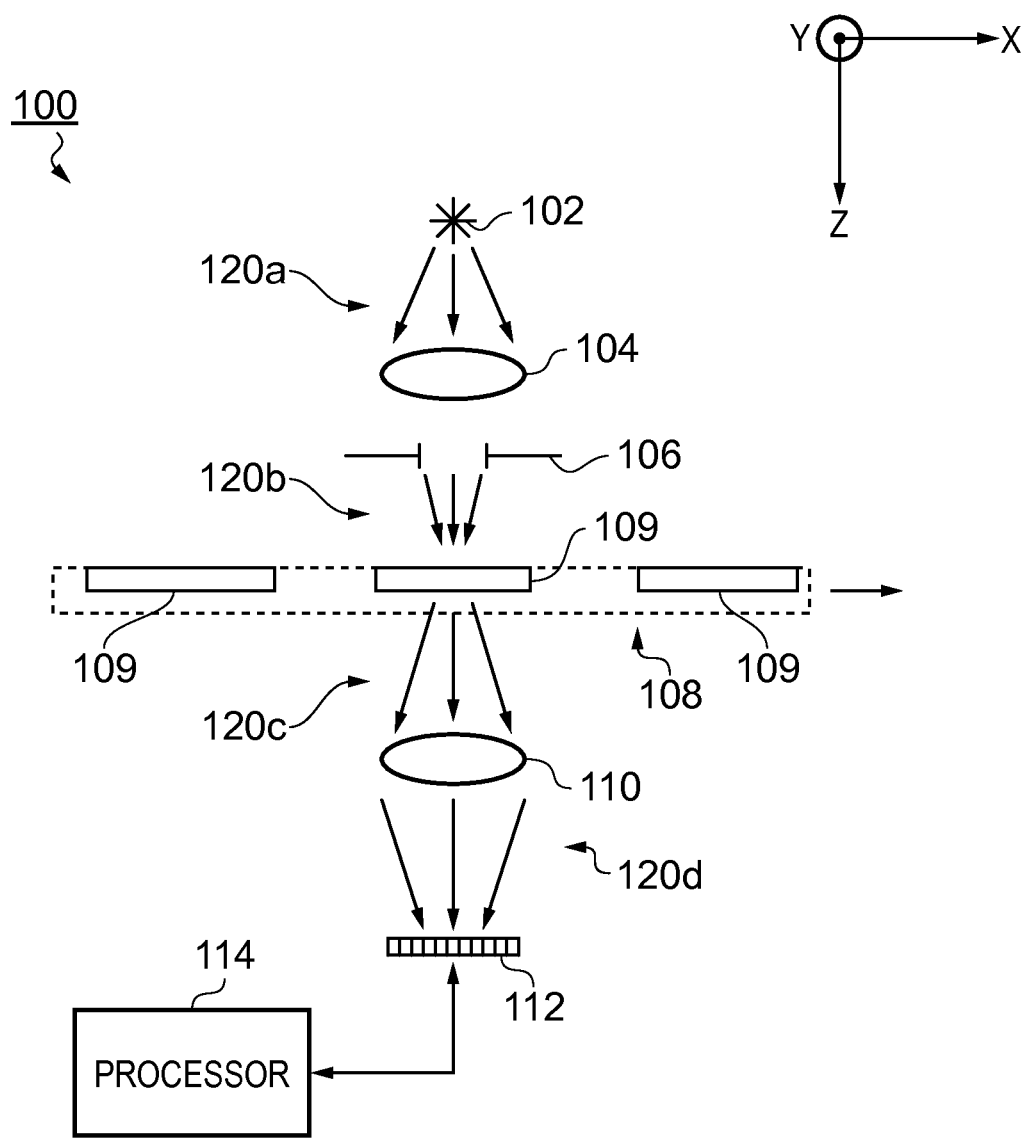
FIG. 1 shows an apparatus for automated high-content screening (HCS) of one or more multi-parameter data sets in accordance with an embodiment of the present invention.

FIG. 1 shows an apparatus 100 for automated high-content screening (HCS) of one or more multi-parameter data sets in accordance with an embodiment of the present invention. The apparatus 100, which is illustrated schematically for clarity, comprises a light source 102 for producing light 120a.

The light 120a is focussed by a condenser 104 onto a test plate 108. The test plate 108 may contain an array of wells or spots 109 to be imaged. The condenser 104 can focus the light 120b in a focal plane at the test plate 108. The test plate 108 may be provided as a consumable product, and the spots 109 might contain various materials that are able to interact with certain types of cells (e.g. mammalian cells).

In various embodiments, the test plate 108 may comprise at least one fiducial marker (not shown) provided to aid in aligning the test plate 108 within the apparatus 100. For example, one or more coloured dyes may be provided within the spots 109. Such coloured dyes can be identified by various imaging systems in order to derive data relating to the relative positioning of the test plate 108 within the apparatus 100. For example, the apparatus 100 may be a GE INCELL ANALYZER 1000™ that is commercially available from GE Healthcare Life Sciences, Little Chalfont, Buckinghamshire, U.K., and which can use four colour channels to image the test plate 108. One colour channel may thus be dedicated to imaging coloured fiducial markers provided in various of the spots 109 in order to obtain data relating to the positioning of the test plate 108 within the apparatus 100.

The apparatus 100 also contains a detector system 112 and a translation mechanism (not shown). The translation mechanism is configured to move the focus of the light 120b relative to the test plate 108 (e.g. by moving the test plate 108 in the x-y plane). This enables a plurality of images to be acquired from respective of the individual spots 109. Additionally, the translation mechanism may also be operable to move the test plate 108 in the z-direction shown in FIG. 1, for example, in order to bring the spots 109 into focus.

For certain embodiments, only one spot is imaged at a time. The images acquired are of sufficient magnification to resolve cells and sub-cellular morphology. With the current GE INCELL ANALYZER 1000™, this may entail use of a 20× objective, the field of view of which is slightly smaller than a single spot. However, various methods of the invention would also work for lower power magnification imaging, e.g. on GE INCELL ANALYZER 1000™ using a 4× objective to image 4-6 spots/image.

An aperture stop 106 is optionally provided between the light source 102 and the detector system 112, the size of which may be variable. For example, various differently sized movable apertures may be rotated into position or a continuously variable iris-type diaphragm may be provided. Image contrast can be controlled by changing the aperture setting of the aperture stop 106.

Focussed light 120b passing through the aperture stop 106 passes through the sample test plate 108 in a transmission imaging mode. Emergent light 120c modulated with image information relating to material adjacent to an individual spot 109 is collected by an objective lens 110 and focussed 120d onto the detector system 112, and is used to form an original image for that spot 109.

Various embodiments of methods of the present invention are independent of the imaging modality used, e.g. they can operate with transmission or reflection geometry. For GE INCELL ANALYZER 1000™ imaging an epi-fluorescence mode may be used, with both the fiducial marker spots and the assay signals from the cells being imaged at different excitation and emission wavelengths. However there is nothing in principle to prevent a mix of imaging modes being deployed, provided that they do not interfere. For example, it would be possible to use a non-fluorescent dye for fiducial marking and to detect the fiducial marks by absorbance in reflectance or transmission geometry, while detecting assay signals by epi-fluorescence.

The detector system 112 is operable to acquire a plurality of images from the test plate 108, each image may be represented in electronic form as a respective multi-parameter data set. For example, several multi-parameter data sets may be obtained each representing an image of respective different spots 109 or of the same spot 109 at different points in time. Differences between neighbouring spots 109 or temporal changes occurring within the same spot 109 can thus be analysed.

The detector system 112 is also operably coupled to a processor 114 that in turn is operable to process the multi-parameter data sets. The processor 114 is operable to measure correlation between pairs of parameters within a multi-parameter data set. For example, parameters such as cell perimeter, diameter, ellipticity, etc. may be assessed in a pair-wise fashion to determine a quantified degree of correlation therebetween.

The processor 114 is then operable to modify correlated parameter values within a predetermined multi-parameter data analysis set for the multi-parameter data set to form an analysis parameter set. The predetermined multi-parameter data analysis set may, for example, contain a list of all parameters that can be measured for a particular cell image. Such a list may then, for example, be pruned by the processor 114 to remove one of a pair of parameters having a correlation threshold greater than a predetermined value. For example, the processor 114 may determine that a cell feature's perimeter and diameter have a correlation greater than 95% and thus remove perimeter as a parameter to be determined from the multi-parameter data set. An appropriately revised list of parameters to be determined is stored as the analysis parameter set.

The processor 114 is also operable to analyse the multi-parameter data set using the analysis parameter set to identify one or more phenotypes from the multi-parameter data set. For example, the processor 114 may sequentially determine a value for each parameter in the analysis parameter set for each appropriate cell feature. Where such a cell feature occurs many times in an image defined by a multi-parameter data set, any pruning of the original predetermined multi-parameter data analysis set ensures that data processing overheads are reduced. Analysis of the multi-parameter data set is thereby quickened. Additionally, identification of various features is also statistically improved by the removal of any correlated parameters from the final multi-parameter data set analysis. Moreover, such a technique also provides dynamic/automatic modification of the parameters used for data analysis such that they are not necessarily predetermined but can instead adapt to the data that is being analysed.

The processor 114 may be further operable to identify one or more phenotypes from a plurality of multi-parameter data sets and compare respective phenotypes from the multi-parameter data sets to identify variations therebetween. For example, the processor 114 may be used to compare phenotypes from one image to those of another image. Such a technique enables control samples of cells provided at the spots 109 to be compared to similar but treated cells provided at others of the spots 109.

An advantageous option for the apparatus 100 is to provide a processor 114 that is further operable to form one or more respective analysis parameter sets for a plurality of multi-parameter data sets, and to compare the analysis parameter sets to determine whether or not a correlation relationship is maintained between the multi-parameter data sets. By determining whether spatial (e.g. across an array of spots 109) and/or temporal variations in the correlation between various parameters occurs, extra information that is not conventionally available can be obtained.

For example, a cell nucleus may die (e.g. via apoptosis) and split into small fragments. These may generally have the same overall shape (e.g. round/ovoid/etc.). In this case, the parameters relating to imaged diameter and perimeter will have a relatively high degree of correlation for both the initial cell nucleus and the fragments. However, during the apoptosis process, the nucleus may change shape into a stellate (star-like) form, and in this latter form a measurement of correlation between the parameters relating to diameter and perimeter will drop. Hence by monitoring the level of correlation between various phenotypes, additional potentially useful information relating to various biological processes can be obtained.

In various embodiments, correlation may be determined by using a non-parametric statistical pair-wise measurement made between the phenotypes in the predetermined multi-parameter data analysis set. For example, a Kolmogorov-Smirnov (KS) distance measurement analysis, as is described in further detail below, may be used. Use of the KS distance measurement analysis technique is preferred in certain embodiments as it is relatively fast. However, those skilled in the art will be aware that various other correlation measurement techniques could instead be used.

Additionally, the processor 114 can be configured to control a translation mechanism (not shown) to move the focal position of the light source 102 relative to the spot plate 108. The processor 114 may, for example, be provided as part of a conventional computer system appropriately programmed to perform such tasks, or may be provided by a digital signal processor (DSP), dedicated application specific integrated circuit (ASIC), appropriately configured firmware, etc.

The apparatus 100 of various embodiments of the present invention may comprise a microscope with one or more cameras and a processor 114 that can be used as a high-content screening apparatus. Images represented by one or more multi-parameter data sets may be generated by the apparatus 100, or may provided from storage, transmitted etc. to the processor 114, for automatic analysis. Various ways for providing such automated analysis are described in greater detail below by way of non-limiting example.

Figure 2:
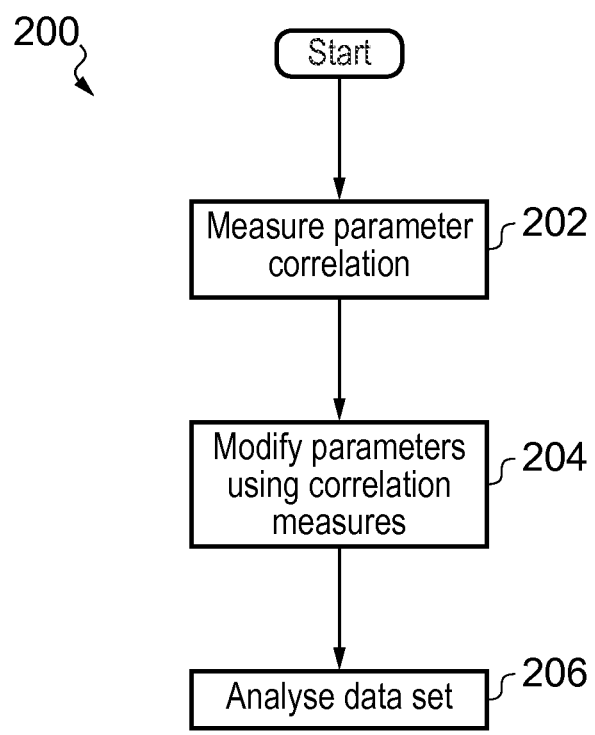
FIG. 2 shows a method for identifying one or more phenotypes from a multi-parameter data set in accordance with various aspects of the present invention.

FIG. 2 shows a method 200 for identifying one or more phenotypes from a multi-parameter data set in accordance with various aspects of the present invention. The multi-parameter data set may include data corresponding to an image provided, for example, using an apparatus 100 of the type described in connection with FIG. 1, above.

The method 200 includes the step 202 of measuring correlation between pairs of parameters within the multi-parameter data set. Then at step 204 correlated parameters from within a predetermined multi-parameter data analysis set are modified to form an analysis parameter set.

Modification of correlated parameter values may comprise multiplication or other arithmetic modification of the parameter values using one or more factors derived from correlation measurements, including modification of the parameter value to zero, or removal of the parameter completely from further analysis, for example.

At step 206 the multi-parameter data set is analysed using the analysis parameter set to identify one or more phenotypes from the multi-parameter data set. Various techniques for providing the functionality of method 200 are described in greater detail below.

The method 200 may be used to determine whether changes occur between multi-parameter data analysis sets. For example, the method 200 can be used to detect drug induced-effects over time. These effects might be qualifiable/quantifiable, and may include phenomena and processes such as changes in size parameters, necrosis, mitosis (cell splitting) etc.

The method 200 can be used for automated image analysis e.g. in high-throughput screening (HTS) for drug assays or the like. The multi-parameter data set may comprise cellular data such as a microscope image. In various aspects of the present invention, and in contrast to conventional methods, data testing may be performed on an inter-data set basis rather than an intra-data set basis.

The method 200 may be applied to images that have been previously stored, transmitted etc., or may acquired and processed "on-the-fly". The method 200 may be implemented using a processor comprising one or more of hardware, firmware and software. For example, the processor might use a conventional personal computer (PC), ASIC, DSP, etc., and/or the apparatus may include a GE INCELL ANALYZER 1000™ using GE's INCELL MINER™ software package upgraded to implement the method 200. Additional functionality, as described herein, may also be provided by various embodiments that implement the method 200.

In various embodiments of the present invention, the method 200 can be implemented by an apparatus using various software components. Such software components may be provided to an apparatus in the form of an upgrade, for example, transmitted to the apparatus via the Internet.

Figure 3:
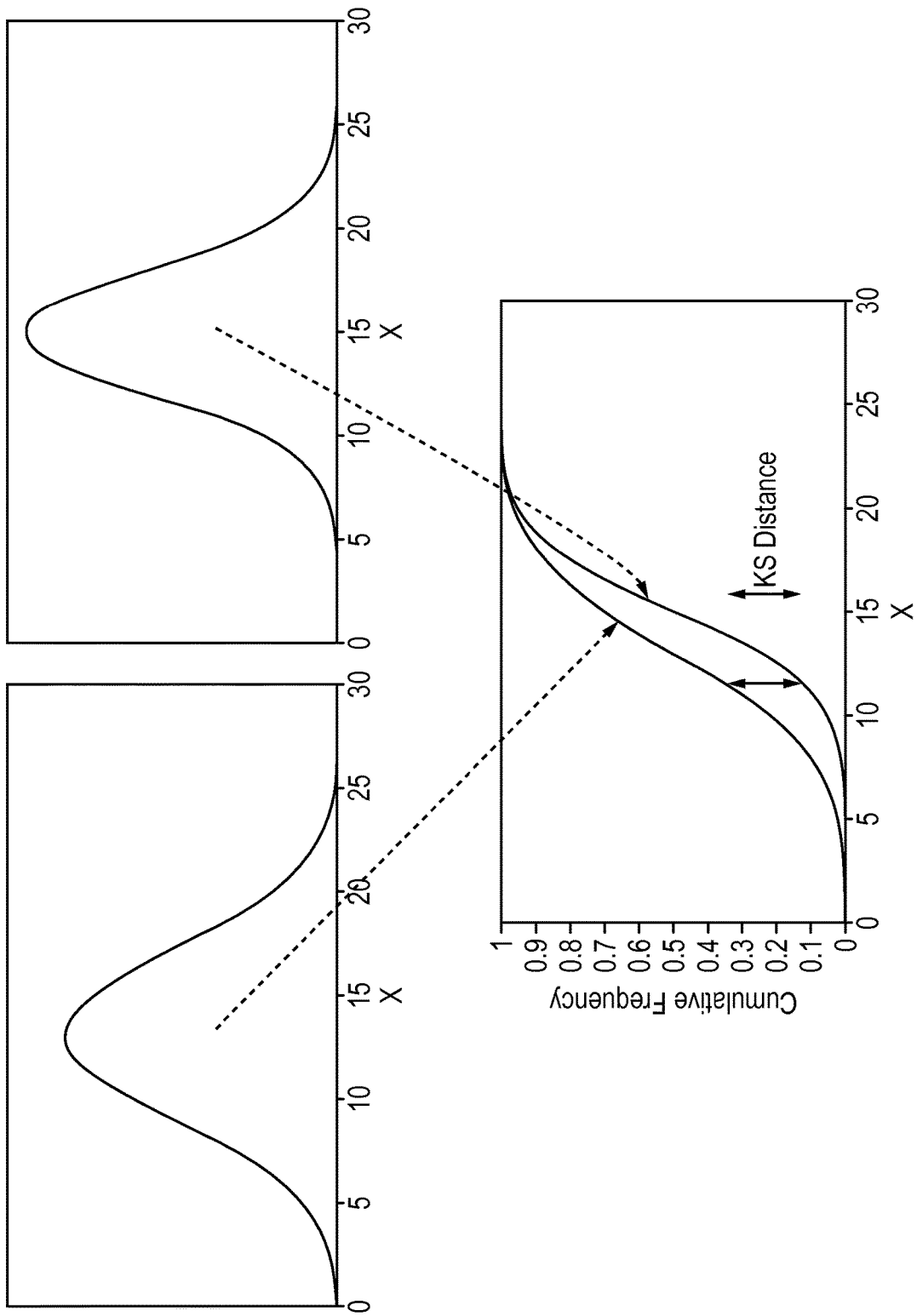
FIG. 3 illustrates the principle of determining the Kolmogorov-Smirnov (KS) distance between two data populations in accordance with various embodiments of the present invention.

FIG. 3 illustrates the principle of determining the Kolmogorov-Smirnov (KS) distance between two data populations in accordance with various embodiments of the present invention.

For example, the method of Altschuler et al may be used, although it does not itself teach the use of inter-sample KS distances for detecting correlation between parameters, nor use of inter-sample KS distance measures in combination with intra-sample distance measures for the purposes of producing summary scores to detect phenotypic changes across a range of parameters.

KS distance measurements are readily generated by comparison of the frequency distribution of data within two data sets, as seen in FIG. 3. Conversion of standard distribution histograms (data graphed as count or frequency of data points (i.e. cells) for a given data value) to cumulative frequency distribution curves (data graphed as cumulative fraction of data for a given data value) allows two populations of data with complex distributions to be compared as similar functions and the difference in distributions expressed as the maximum vertical distance between the cumulative frequency functions; the KS distance.

Since KS distance measurement may be used without prior knowledge of the normality or non-normality in the distribution of an analysis parameter across a cell population, and may be used for comparing datasets of unequal size, e.g. data from two cell populations comprising different numbers of cells, use of KS distance provides an un-biased comparative measure of differences in data derived from two cell populations, and has been shown to significantly improve data quality from HCS assays.

Use of KS distance or other non-parametric comparators allows highly complex HCS datasets comprising many different parameters to be analysed and allow for example the effects of dose and/or time of exposure of a compound on cells to be accurately measured by use of the distance measure to determine whether data from two populations, e.g. control and drug treated cells differ significantly.

A common problem occurring in HCS in acquisition of multi-parameter data is determining amongst the many quantitative parameters abstracted by image analysis which are independent parameters (i.e. those parameters which are related to and measuring different cellular phenomena) and which are correlated parameters (i.e. those parameters which are related to and measuring the same cellular phenomena). For example in morphological measurements of cell nuclei certain parameters might be expected to be correlated; nuclear area, length and perimeter measurements all relate to a single object and are related geometrically. In less simple cases pairs or groups of parameters may be measuring the same cellular phenomena by different means not apparent to the investigator and hence be directly or indirectly correlated. There is therefore a need to distinguish between measurement parameters which are mathematically correlated and those which are biologically correlated.

Undetected data correlation is a significant issue for multi-parameter assays, which are becoming standard in HCA, the increased data depth requires multiple KS distance measures to define phenotypic differences, where a cellular phenotype may be described and defined using a phenotypic signature comprising a series of KS distance measures in different parameters relative to a control population. In such cases problems may arise in interpretation of data, since a phenotypic change may be detected in a number of parameters without knowledge of underlying correlation between parameters. This may lead to overestimates of phenotypic change, or failure to discriminate between phenotypes, where clustering or other ranking of phenotypes is biased by correlated parameters (i.e. measuring the same cellular phenomena twice via separate parameters).

Correlation of parameters does not necessarily devalue or negate the use of such parameters, provided the presence of a correlation is known. For example, as described above, it would be expected that parameters associated with nuclear morphology might exhibit correlation, e.g. nuclear diameter or length would be correlated to nuclear perimeter. If nuclear shape were invariant, the correlation between the two parameters would be invariant and measurement of one of the parameters would be redundant in providing information on phenotypic changes occurring within a cellular population. However if nuclear shape were to vary with a particular treatment the degree of correlation between the parameters is likely to change; for example, if nuclei were to change from a predominantly circular morphology to a stellate form the close correlation between diameter or length and perimeter would change significantly, the stellate nuclei having a much larger perimeter in relation to diameter or length. Hence knowledge of the correlations between parameters and detection in the change of such correlations adds to the data available to accurately characterise changes in cellular phenotypes from HCS data.

One method according to certain aspects of the present invention seeks to address the problem of parameter correlation in multi-parameter HCA data by performing KS distance, or other applicable population comparator measure calculations, between samples (intra-sample) and additionally within samples (inter-sample). The novel use of inter-sample analysis provides means to:

i) establish whether two or more parameters are correlated;
ii) use a combination of intra-sample and inter-sample distance measures to produce phenotype maps to graphically represent phenotypic signatures based on multi-parameter data;
iii) use inter-sample measurements to weight and prioritise data produced from intra-sample measurements and produce a single phenotype score measure summarising the cumulative difference between two cellular populations across a range of measured parameters; and iv) provide additional phenotype characterisation data by measurement of changes in parameter correlation using inter-sample distance measures.

Figure 4:
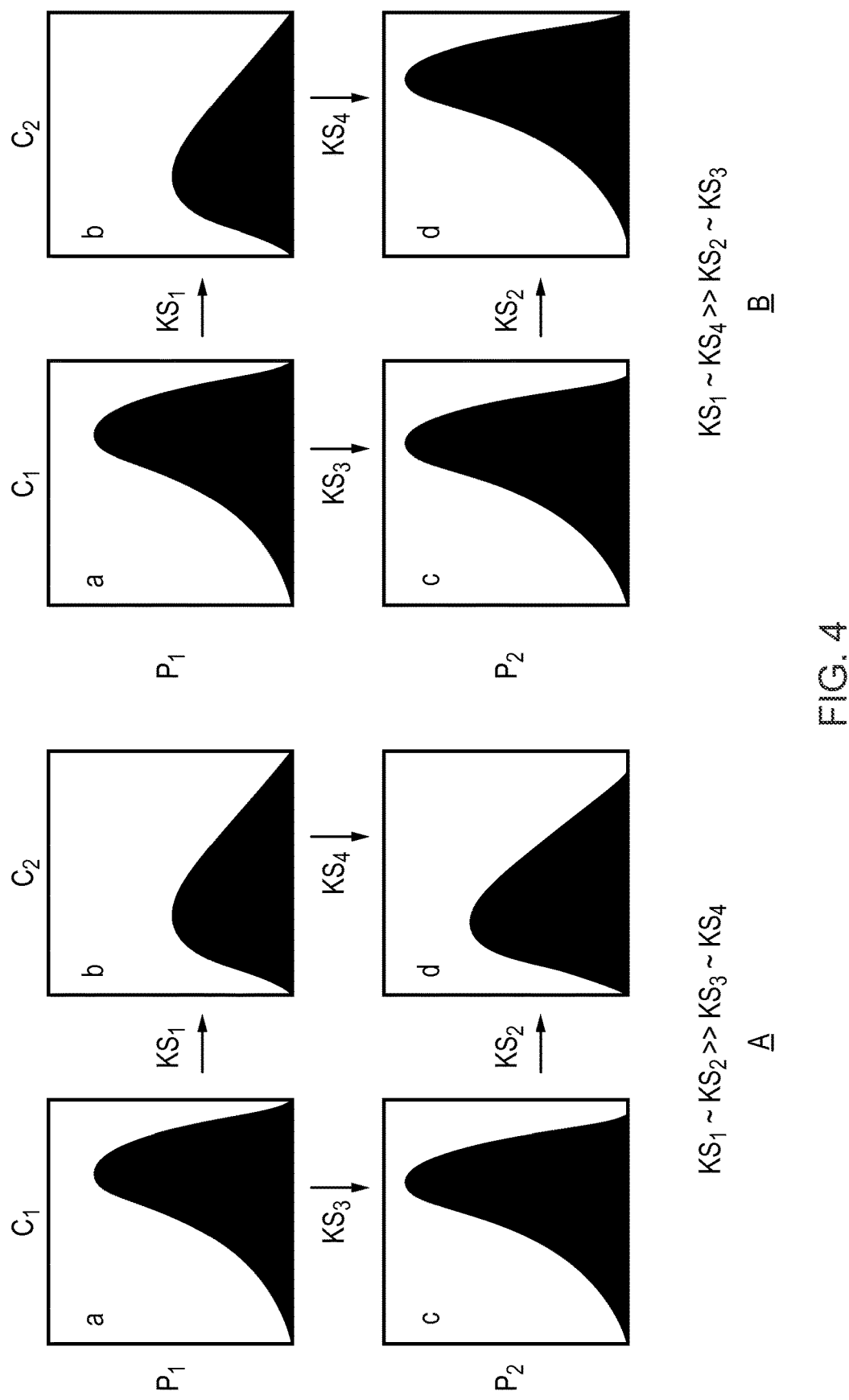
FIG. 4 shows an illustration of intra-sample and inter-sample KS distance determinations as used in various embodiments of the present invention.

FIG. 4 shows an illustration of intra-sample and inter-sample KS distance determinations as used in various embodiments of the present invention.

When using KS distance, or other non-parametric population comparators, it is standard practice to calculate KS distance between a test and control sample, e.g. between data derived from a cell population exposed to a drug and an equivalent population of cells in the absence of the drug. In a typical investigation this may involve exposing populations of cells to increasing concentrations of a test substance and separately calculating a series of KS distances for each treated population relative to a control population.

Such an approach is illustrated in FIG. 4 where cell populations under two conditions ($C_1$ and $C_2$) are analysed for two parameters ($P_1$ and $P_2$) and the intra-sample KS distances for the two parameters are calculated ($KS_1$ and $KS_2$). Depending on the nature of phenotypic changes occurring in the samples between conditions $C_1$ and $C_2$ the intra-sample KS values for the parameters will vary accordingly. In scenario A where the distribution of parameters vary significantly between $C_1$ and $C_2$ both $KS_1$ and $KS_2$ will be high. In scenario B where the distribution of $P_1$ varies significantly between $C_1$ and $C_2$, but the distribution $P_2$ of is not significantly changed, $KS_1$ will be high and $KS_2$ low. Such measurements reflect standard practice and allow quantitative measurement of the changes in cellular parameters arising in cell population under test conditions.

A frequently encountered problem with the conventional method of analysis is that intra-sample KS distances ($KS_1$ and $KS_2$), while providing information on the differences in distributions of individual parameters between test and control samples, give no indication of whether two parameters show correlation and hence may be measuring the same phenomena and so introducing redundancy into the analysis. This case is illustrated in scenario A where both $KS_1$ and $KS_2$ will give high values, but in isolation give no indication of whether the two distance measures relate to the same or different cellular phenomena.

In the method of certain aspects of the present invention, the use of intra-sample distance measures (i.e. comparison of distribution of the same parameter under different treatment conditions), which may comprise KS distance or other suitable non-parametric distance measures, is enhanced by the use of additional inter-sample distance measures to compare the distributions of different parameters in the same sample (i.e. comparison of distribution of different parameters under the same treatment conditions).

These inter-sample measurements are indicated in FIG. 4 as $KS_3$ and $KS_4$ and provide means for determining the degree of correlation between measurement parameters $P_1$ and $P_2$ under conditions $C_1$ and $C_2$. In scenario A where the distribution of both parameters $P_1$ and $P_2$ change between $C_1$ and $C_2$, but where both parameters have similar distributions in $C_1$ and $C_2$ suggesting a degree of correlation, measurement of inter-sample KS distances $KS_3$ and $KS_4$ provides means for testing for such correlation. In this scenario, the relationship between intra-sample and inter-sample KS distance values is:

$$KS_1 \approx KS_2 >> KS_3 \approx KS_4 \qquad \text{Equation (1)}$$

wherein for intra-sample measurements the high values of $KS_1$ and $KS_2$ indicate a significant change in both parameters between $C_1$ and $C_2$, while the low $KS_3$ and $KS_4$ values for inter-sample measurements indicate that the difference between the distributions of the two parameters at both $C_1$ and $C_2$ are similar indicating a high degree of correlation between $P_1$ and $P_2$.

In contrast, in scenario B only the distribution of $P_1$ changes significantly between $C_1$ and $C_2$ while $P_2$ retains substantially the same distribution. In this scenario, the relationship between intra-sample and inter-sample KS distance values is:

$$KS_1 \approx KS_4 >> KS_2 \approx KS_3 \qquad \text{Equation (2)}$$

wherein for intra-sample measurements the high values of $KS_1$ indicate a significant change in the distribution of $P_1$ between $C_1$ and $C_2$ and the low value of $KS_2$ indicates conservation of the distribution of $P_2$ between $C_1$ and $C_2$, where for inter-sample measurements the low $KS_3$ value indicates a similar distribution in $P_1$ and $P_2$ which may be indicative of correlation in these parameters at $C_1$, and the high value for $KS_4$ indicates the absence of correlation between $P_1$ and $P_2$ at $C_2$.

Consequently combination of intra-sample and inter-sample distance measures by a method in accordance with various aspects of the present invention provides new ways for:

i) testing for correlation between parameters (detection of low inter-sample KS distances at all conditions); and ii) highlighting changes in parameter correlation between conditions (detection of inter-sample KS distances varying across conditions).

The first aspect is important in optimising data collection in HCS; collection of correlated data (i.e. data describing the same phenomena by different means) is a redundant activity and wastes data storage and processing time. The second aspect is important in maximising the information content of HCS data; information that two parameters are changing correlation can yield additional information from existing parameters (e.g. variance in the correlation in object dimensional parameters can yield information relating to changes in object morphology not apparent from the individual parameters).

It will be clear to those skilled in the art that further scenarios involving differing behaviour between two parameters are possible wherein the two parameters exhibit varying degrees of change in distribution and correlation either under two conditions as described above or under a larger series of conditions where the different conditions may represent cellular populations exposed to different substances, concentrations of substances, for different times or other varying conditions alone or in combination, such as might be encountered in a large scale HCS screening program. Furthermore it will be appreciated by those skilled in the art that the same principles embodied in aspects of the present invention when combining intra-sample and inter-sample analysis may be applied to greater than two parameters, with a geometric increase in the number of pair-wise comparisons possible for inter-sample distance calculations.

Figure 5:
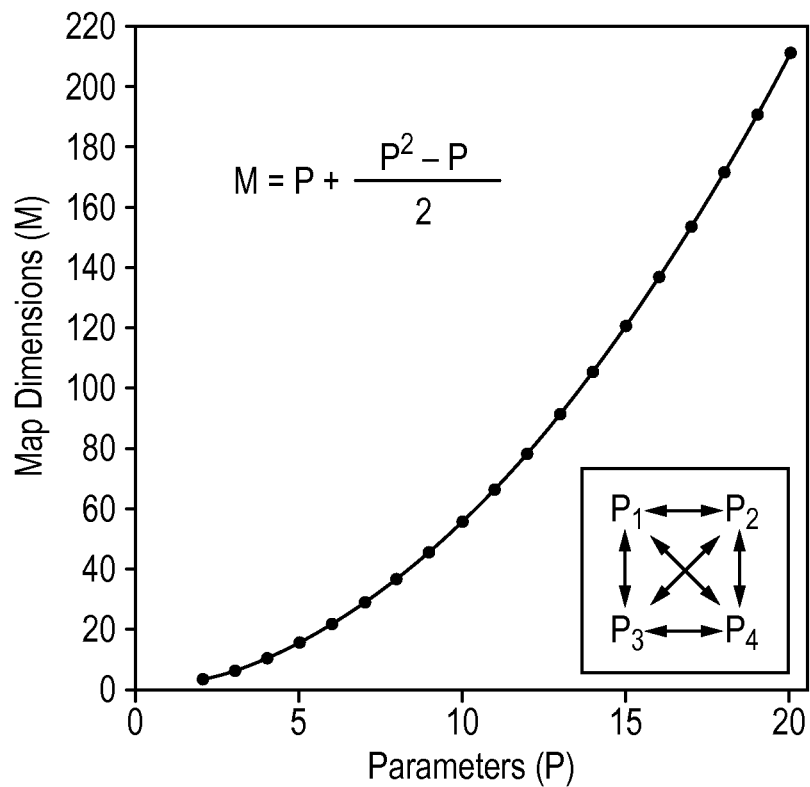
FIG. 5 shows the relationship between data parameters and phenotype map dimensions in an embodiment of the present invention.
Figure 5:
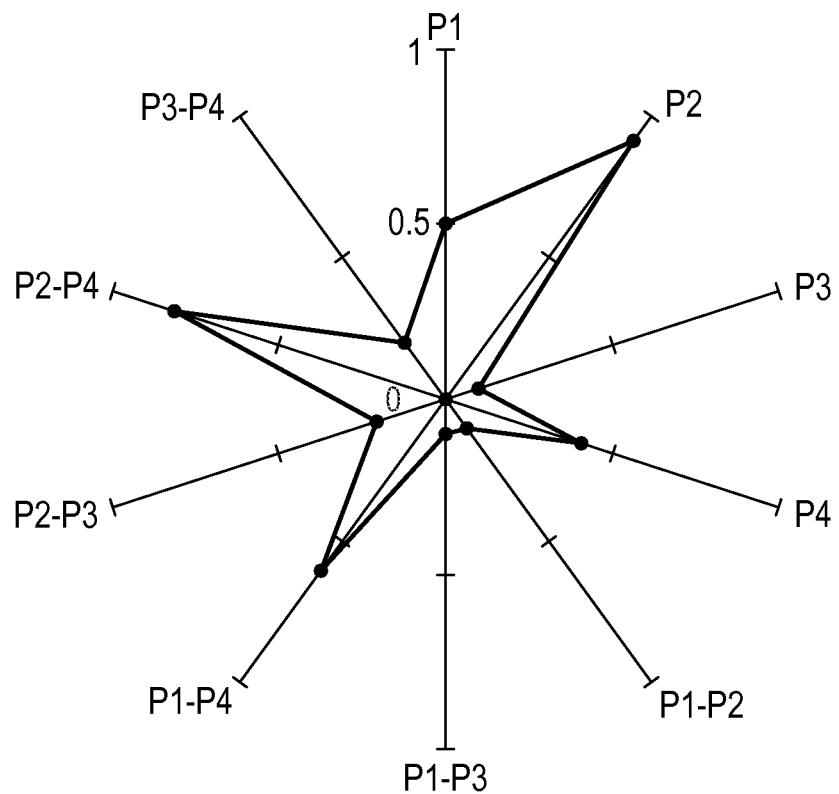

FIG. 5 shows the relationship between data parameters and phenotype map dimensions in an embodiment of the present invention.

The application of one method according to an embodiment of the invention to larger datasets is illustrated in FIG. 5. For any set of HCS parameters of where the number of parameters is P, the number of available pair wise inter-sample distance measurements is:

$$\frac{P^2 - P}{2} \quad \text{Equation (3)}$$

Combining these inter-sample distance measurements for all P parameters (i.e. all distances between the distributions of each parameter at a given treatment condition) with intra-sample distance measurements (i.e. all distances between the distributions of individual parameters at a given treatment condition and the distribution of the same parameter under control conditions) yields a total number of distance measurements M:

$$M = P + \frac{P^2 - P}{2} \quad \text{Equation (4)}$$

Where M is the number of dimensions of a graphical representation of the data as a phenotype distance map representing all available distance measures for a set of parameters P and where M increases as a geometric function of P as illustrated in FIG. 5.

A representative phenotype distance map is shown in FIG. 5 for four parameters $P_1$, $P_2$, $P_3$ and $P_4$. Each axis of the map is scaled from 0-1 corresponding to the available range for KS distance measurements and each axis shows the KS distance value for intra-sample measures ($P_1$, $P_2$, $P_3$ and $P_4$) and for the six available inter-sample distance measures ($P_1$-$P_2$, $P_1$-$P_3$, $P_1$-$P_4$, $P_2$-$P_3$, $P_2$-$P_4$ and $P_3$-$P_4$).

EXAMPLES

The following examples serve to illustrate embodiments of the present invention. These examples are intended to demonstrate techniques which the present inventors have found to work well in practising the present invention. Hence these examples are detailed so as to provide those of ordinary skill in the art with a complete disclosure and description of the ways in which the methods of this invention may be performed. The following Examples are intended to be exemplary only and changes, modification and alterations can be employed to the conditions described herein, without departing from the scope of the invention.

Example 1

Generation of Multi-Parameter Cellular Data and Analysis

CHO-K1 cells were seeded into a GE Healthcare 96 well MatriPlate at 6000 cells/well in Ham's F12 media supplemented with 5% EBS and incubated under standard tissue culture conditions for 24 hours. Mitomycin C (MMC) solutions were added in culture media to provide final concentrations in the assay of 0-10 mM and cells incubated for a further 48 hours. Media was removed from wells and cells washed once with 200 ml phosphate buffered saline (PBS), followed by fixation in ethanol for 30 minutes at room temperature. Nuclei were stained with 5 mM HOECHST™ 33342 (Sigma) at room temperature for 15 minutes and cells washed with 200 ml PBS.

Cells were imaged by a GE Healthcare INCELL ANALYZER 1000™ using v3.5 acquisition software (available from GE Healthcare) with a 20× objective. Images were acquired using on-line cell counting to acquire a minimum of 1000 cells/well. Images were analysed for nuclear area, length, perimeter and weighted moment of inertia (WMOI) using GE INCELL INVESTIGATOR™ software (available from GE Healthcare).

Figure 6:
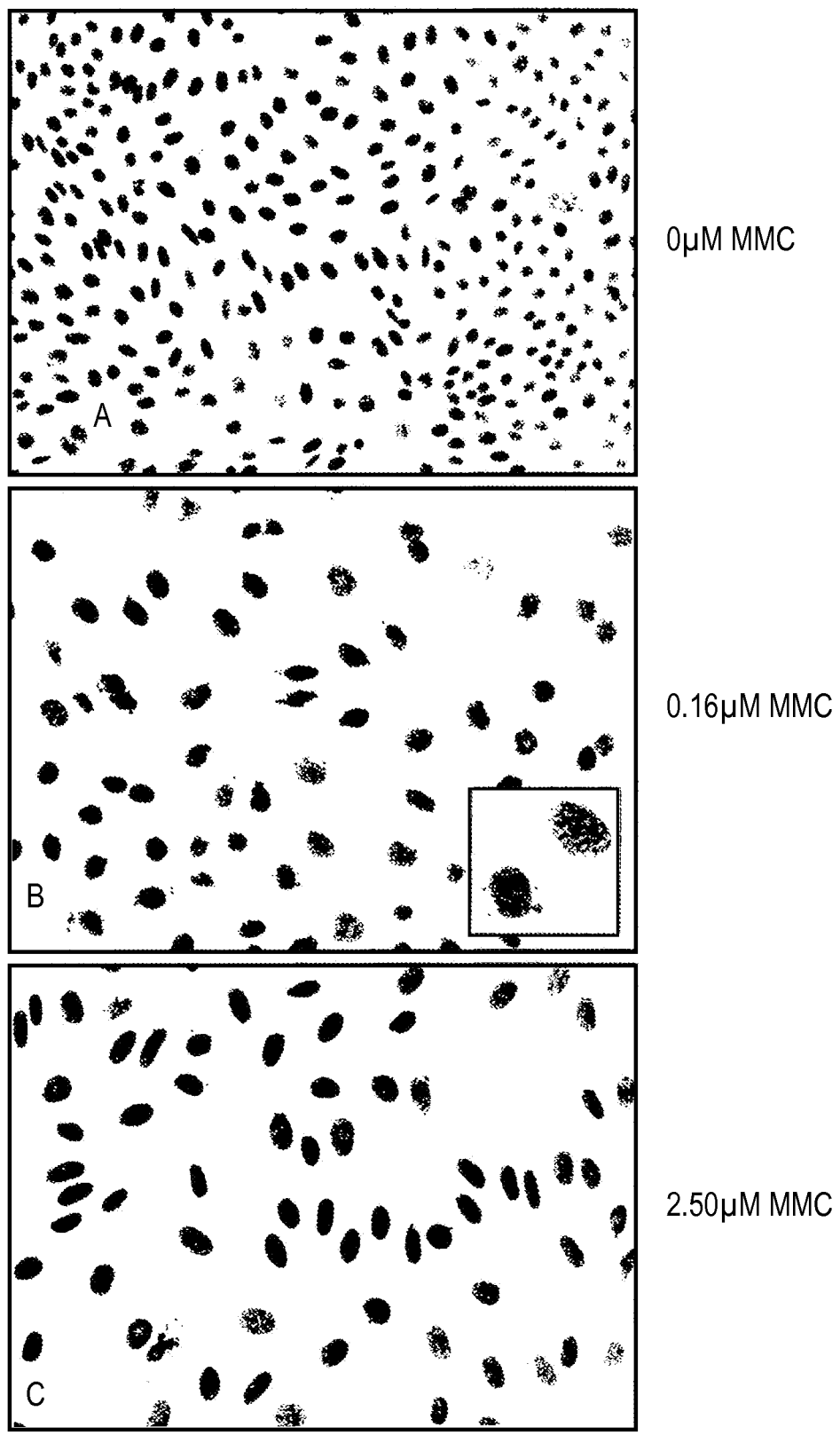
FIG. 6 shows representative images from high-content screening of cells treated with increasing concentrations of Mitomycin C used to derive data for analysis in accordance with an aspect of the present invention.
Figure 7:
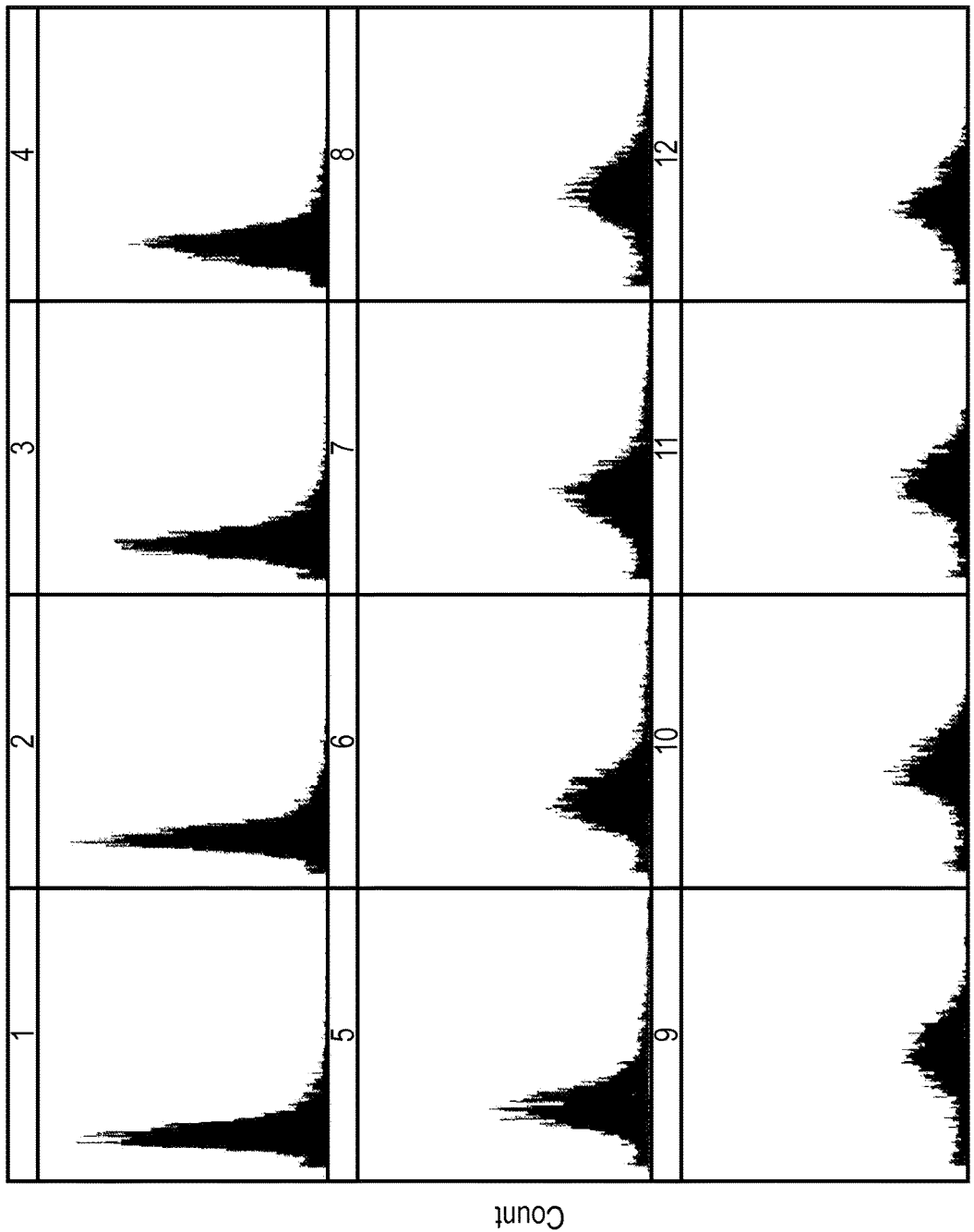
FIG. 7 shows nuclear area data derived from high-content screening of cells treated with increasing concentrations of Mitomycin C used to derive data for analysis in accordance with an aspect of the present invention.
Figure 8:
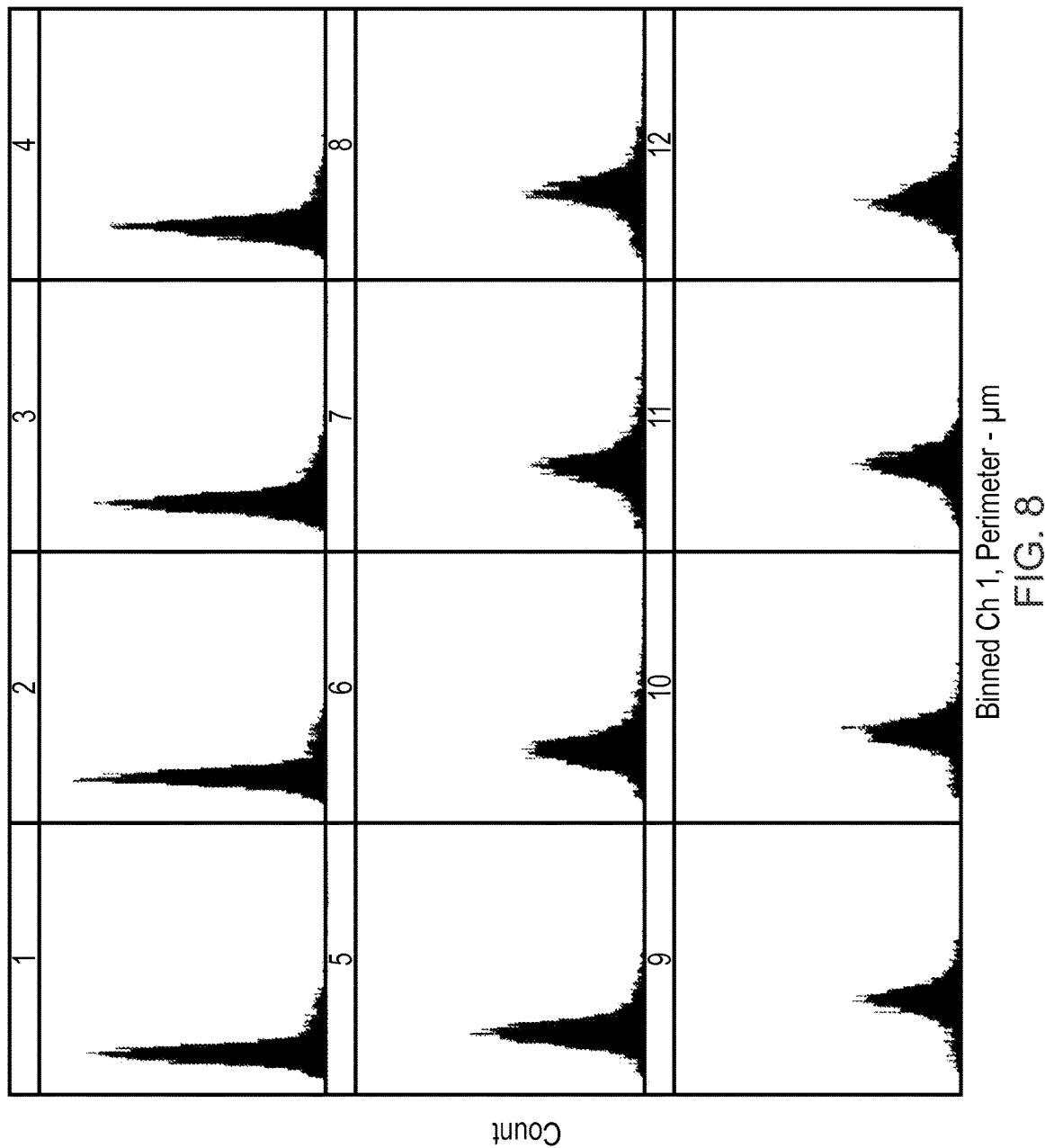
FIG. 8 shows nuclear perimeter data derived from high-content screening of cells treated with increasing concentrations of Mitomycin C used to derive data for analysis in accordance with an aspect of the present invention.
Figure 9:
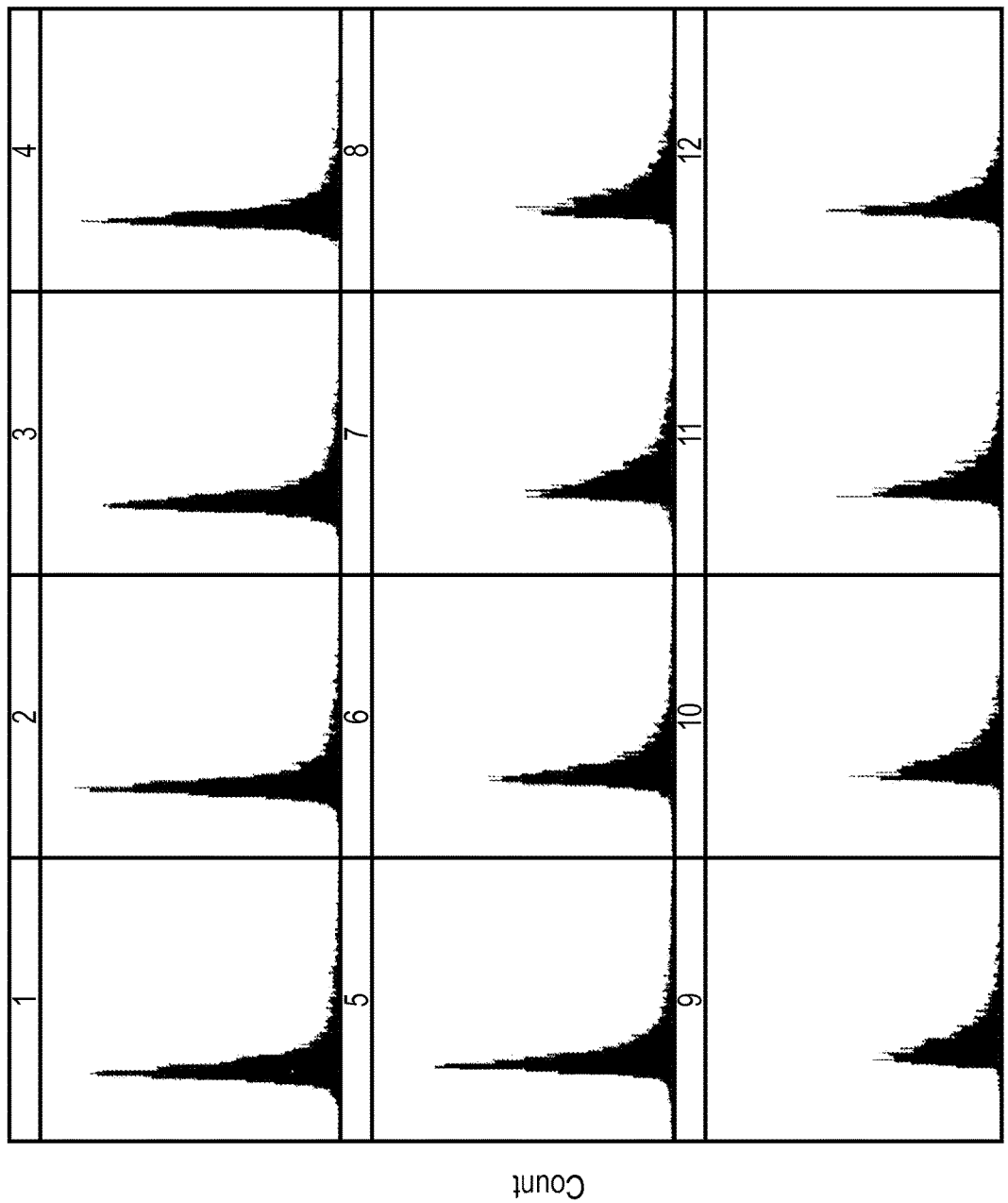
FIG. 9 shows nuclear weighted relative moment of inertia data derived from high-content screening of cells treated with increasing concentrations of Mitomycin C used to derive data for analysis in accordance with an aspect of the present invention.
Figure 10:
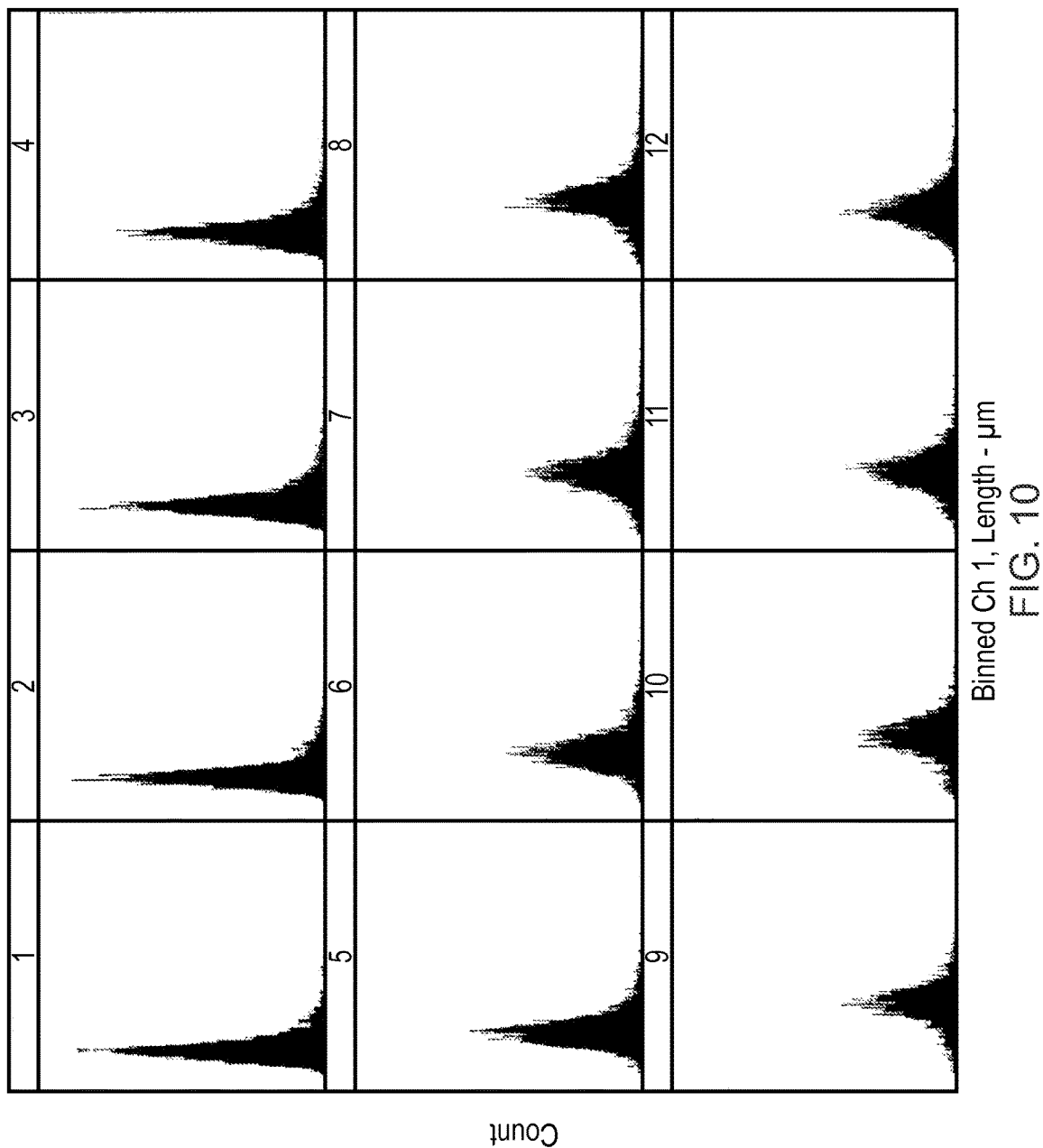
FIG. 10 shows nuclear length data derived from high-content screening of cells treated with increasing concentrations of Mitomycin C used to derive data for analysis in accordance with an aspect of the present invention.

FIG. 6 shows representative images from the high-content screening of cells treated with increasing concentrations of Mitomycin C.

Treatment of cells with MMC, a well known clastogenic agent causing DNA strand breakage leads to significant changes in nuclear morphology including increase in nuclear area associated with cell cycle blockage in the G2 phase of the cell cycle, formation of micronuclei through incorrect segregation of damaged chromosomes at mitosis, and at high concentrations, changes in nuclear shape and texture associated with nuclear fragmentation and breakdown. Changes in nuclear size, shape and morphology are clearly visible in representative images from HCS image acquisition shown in FIG. 6. Images A, B and C show typical nuclear morphology for cells treated with 0, 0.16 and 2.5 µM MMC respectively, and the inset image in image B (0.16 µM MMC) shows a higher magnification view of nuclei with associated micronuclei arising from clastogenic DNA damage.

Four nuclear morphology parameters were abstracted from images using automated image analysis and data from replicate samples exposed to the same concentrations of MMC combined to yield population distribution histograms for each of the four parameters as shown in FIGS. 7 to 10. In each of FIGS. 7 to 10 the data in panel 1 is from control cells, and the data in panels 2-12 from MMC treated cells across the range of 0.01 µM-10 µM MMC.

Figure 11:
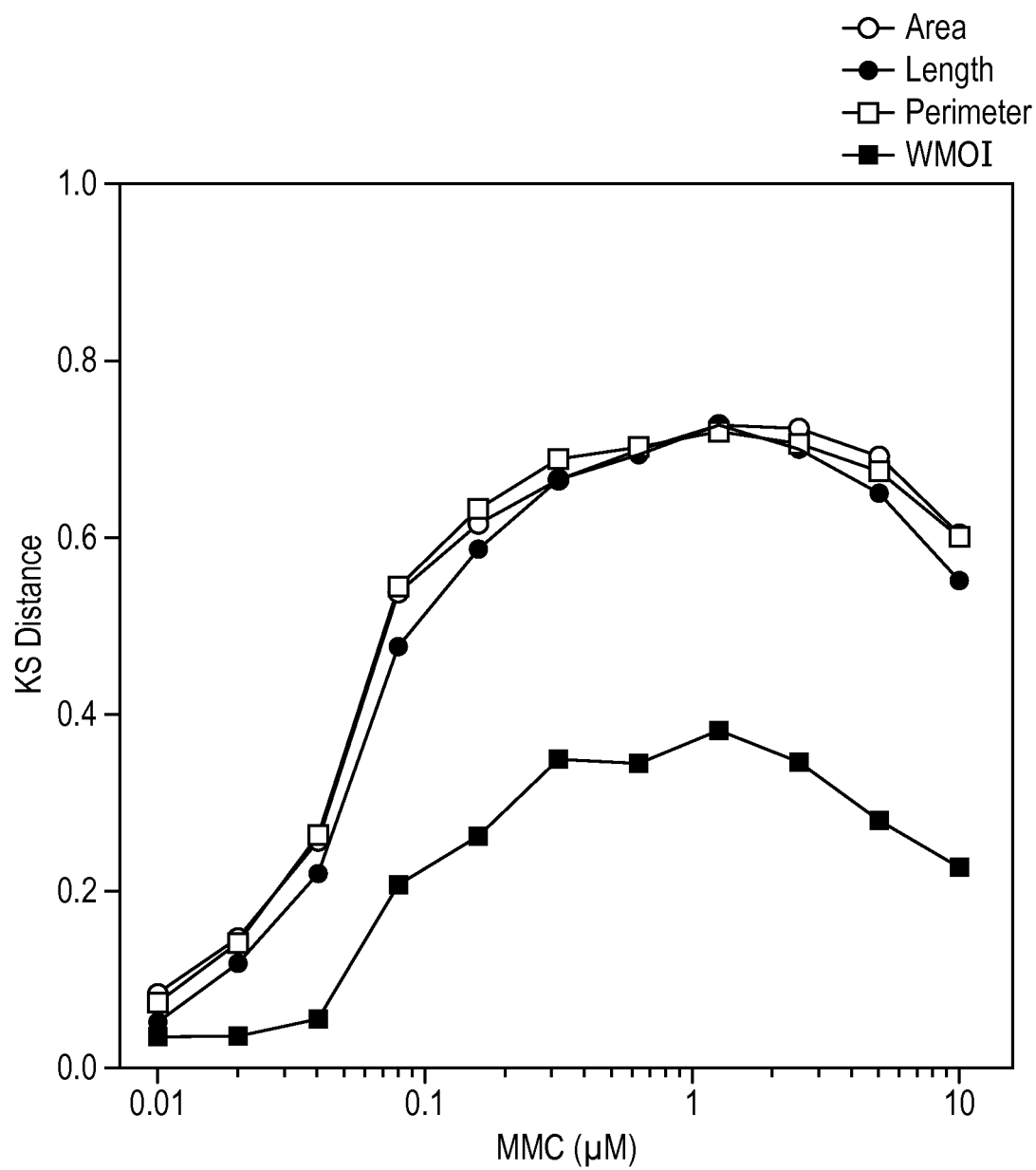
FIG. 11 shows intra-sample KS distance measures data derived from high-content screening of cells treated with increasing concentrations of Mitomycin C in accordance with an aspect of the present invention.

KS distance analysis of the data using intra-sample measurements (i.e. calculation of the KS distance between cell data in the absence of MMC and cell data at a given concentration of MMC across the range 0.01 µM-10 µM) was performed and the resulting data shown in FIG. 11. The data shows a clear dose-dependent increase in KS distances for all four measured parameters indicating a significant dose-dependent change in these parameters relative to untreated cells. Three parameters, nuclear area, length and perimeter showed almost identical KS distances from untreated cells across the whole MMC concentration range. WMOI (a measure of the distribution of the DNA staining pixel intensity values within the nucleus) also showed dose-dependent changes, but to a differing degree to the other three measured parameters.

Inter-sample KS distances were calculated for all six possible parameter pairings (Area-Length; Area-WMOI; Length-WMOI; Area-Perimeter; Length-Perimeter; Perimeter-WMOI) by calculation of KS distance between data distributions for two parameters at the same MMC concentration. In order to perform KS distance measures on the different parameters of which had variant dimensions, parameter values were normalized ($P_{norm}$) to a range from 0-1 using the function:

$$P_{norm} = \frac{P - P_{min}}{P_{max} - P_{min}} \quad \text{Equation (5)}$$

Figure 12:
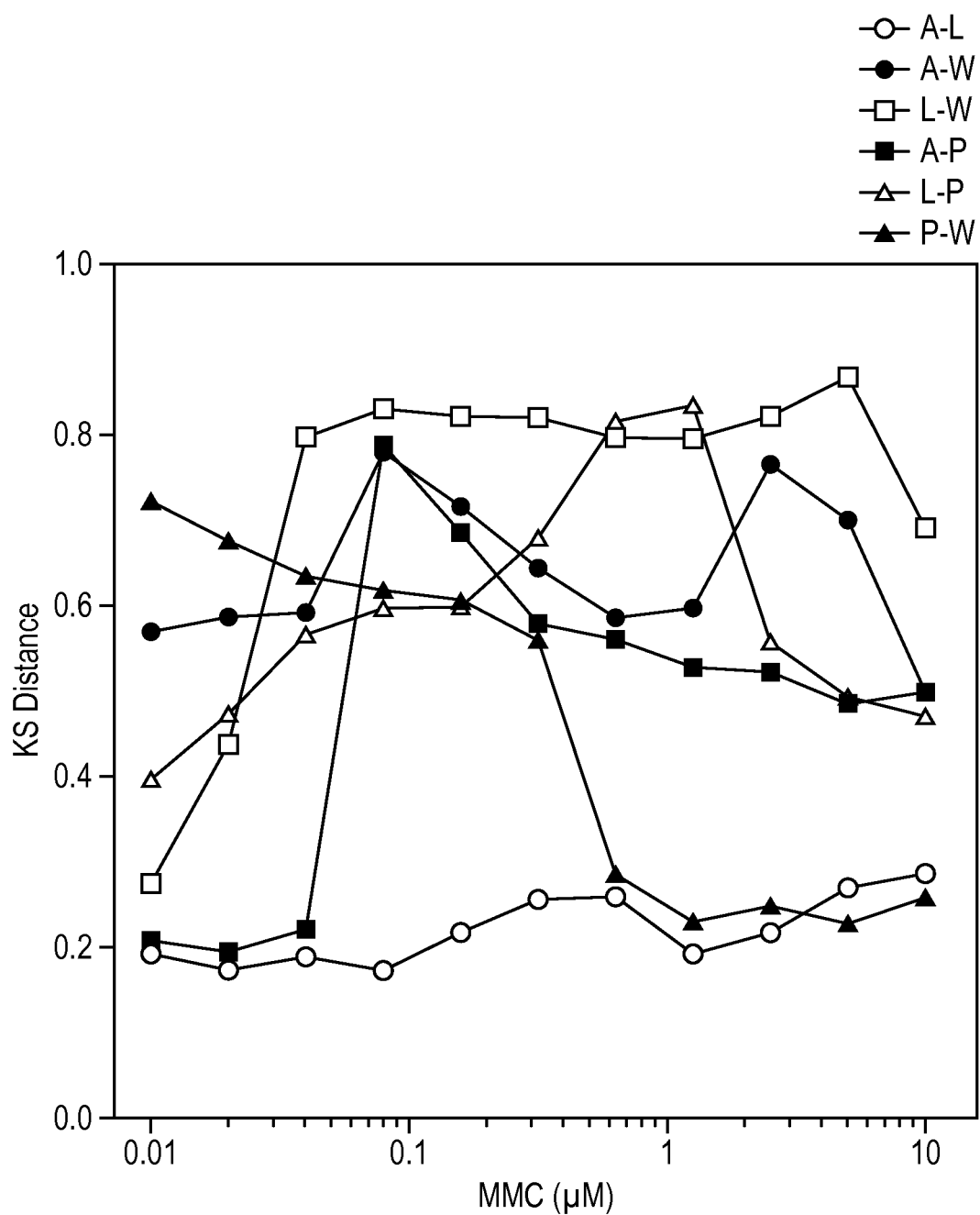
FIG. 12 shows inter-sample KS distance measures data derived from high-content screening of cells treated with increasing concentrations of Mitomycin C in accordance with an aspect of the present invention.

Results for inter-sample KS measurements are shown in FIG. 12 (pair wise distance measures are indicated as follows; A-L Area-Length; A-W Area-WMOI; L-W Length-WMOI; A-P Area-Perimeter; L-P Length-Perimeter; P-W Perimeter-WMOI). The data shows a number of clear patterns in the relationship between parameters revealed by inter-sample KS distance calculations including but not restricted to:

i) Area and length (A-L) show a constant low KS distance across the entire MMC concentration range indicating that these two parameters show similar distributions with a high degree of correlation. Since these two morphological measures are both directly influenced by nuclear size this data indicates that while nuclei are increasing in size on MMC treatment, they are not undergoing morphological changes that change the relationship between area and length (e.g. changing from circular to ovoid);

ii) Length and WMOI (L-W) show a constant high KS distance over most of the MMC concentration range indicating that these two parameters have a low degree of correlation, i.e. DNA intensity distribution within nuclei is not related to nuclear length;

iii) Perimeter and WMOI (P-W) show a dose dependent change in KS distance in an inverse manner to that observed for intra-sample KS distances for these parameters, i.e. the inter-sample KS distance between the distributions of perimeter and WMOI decreases with MMC concentration indicating that these two parameters while not correlated at low dose become correlated at high dose, implying a change in phenotype involving some form of linkage between increasing nuclear perimeter and DNA distribution; and iv) Area and perimeter (A-W) show a low KS inter-sample distance at low and high MMC concentrations with an increase in KS distance at intermediate concentrations, indicating the possibility of two or three phenotype classes occurring at low, medium and high MMC concentrations.

It is well-known that treatment of cells with agents such as MMC that induce DNA damage leads to a complex series of events occurring within cells that results in a range of phenotypes which are related to MMC concentration. At low concentrations cells can repair DNA damage with little or no effect on cell cycle progression and minor variations in nuclear morphology and micronuclei formation. At higher concentrations of MMC the consequently higher levels of DNA damage impose a higher DNA repair burden on cells which results in significant cell cycle delays and an increase in micronuclei formation and other alterations in nuclear structure. At still higher doses of MMC the extent of DNA damage becomes sufficiently high to trigger cells to undergo apoptosis accompanied by gross changes in nuclear morphology and nuclear breakdown.

All of these interrelated processes lead to a very complex series of events occurring in MMC treated cells which impinge directly or indirectly on the observed phenotypes at different concentrations of MMC. The complexity of the events taking place within a large population of cells is not fully apparent from traditional analytical approaches such as analysis of intra-sample population data distribution (FIG. 11). Application of a method in accordance with aspects of the present invention using additional inter-sample population data distribution comparators (FIG. 12) reveals patterns in the data indicative of phenotypic changes which are not apparent in conventional analyses.

Figure 13:
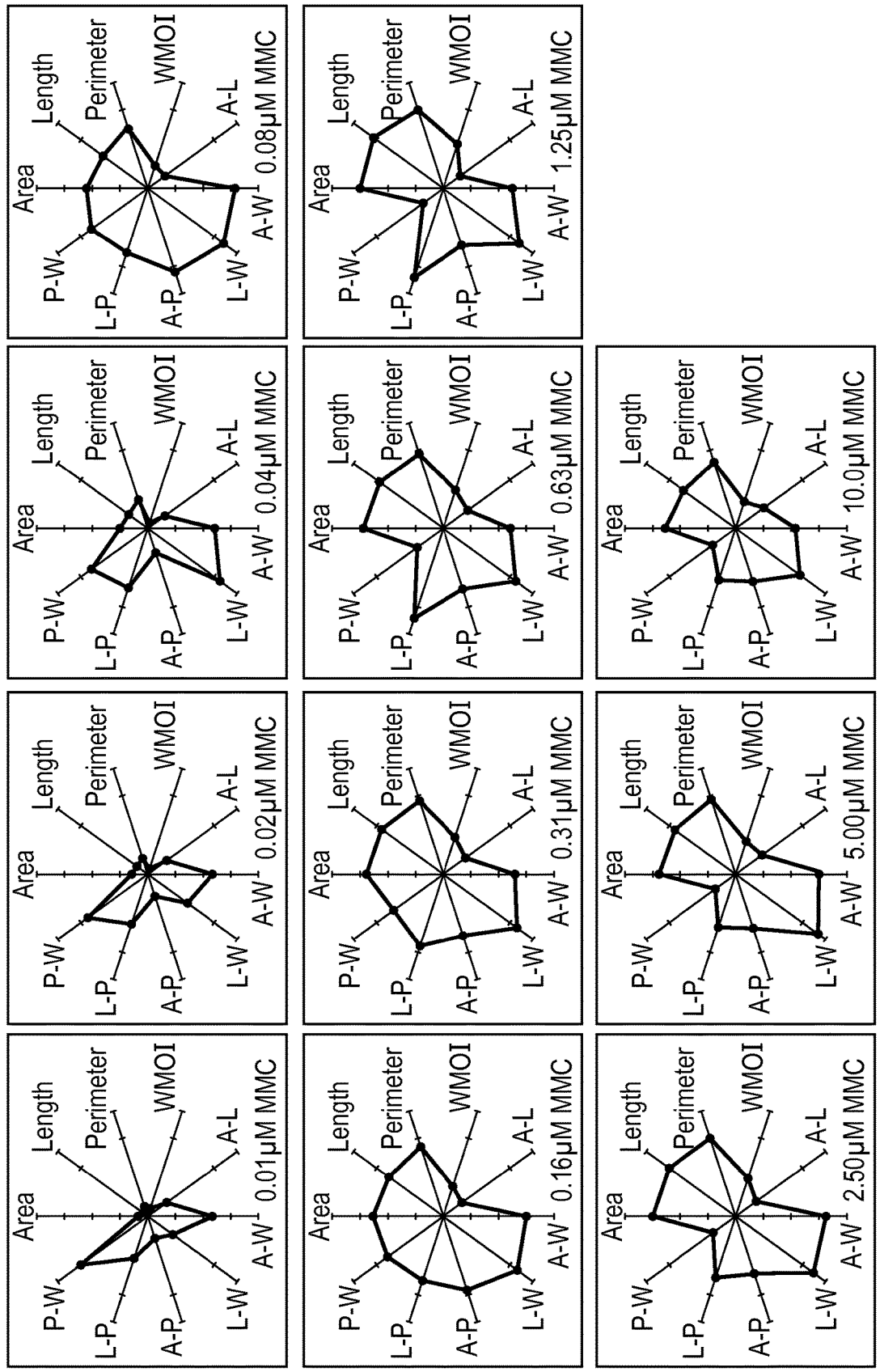
FIG. 13 shows phenotype maps derived from intra-sample and inter-sample KS distance measurements in accordance with an aspect of the present invention.

Combination of intra-sample and inter-sample distance measures may be used to generate phenotype maps (FIG. 13) summarizing the variations and interrelationships in measured parameters at different treatment conditions. Such maps allow rapid visual assimilation of the trends and interrelationships in HCS analysis data not fully apparent from conventional graphical representations such as dose-response plots.

Figure 14:
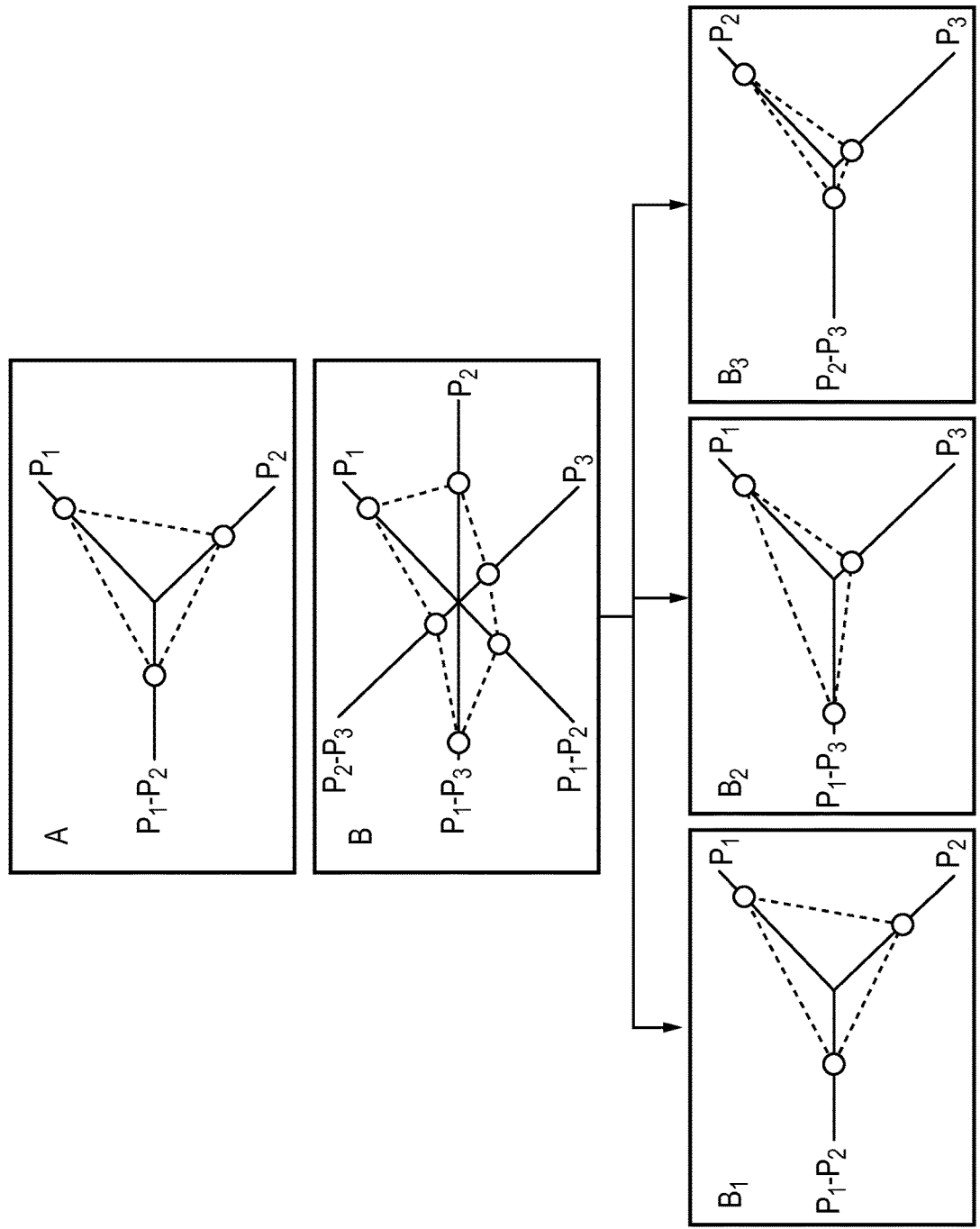
FIG. 14 shows breakdown of phenotype maps into sub-components in accordance with an aspect of the present invention.

As described previously, and illustrated in FIG. 5, the complexity of phenotype distance maps grows geometrically with the number of analysed parameters, however these complex maps may be broken down into a series of simpler elements to aid in further analysis as shown in FIG. 14.

In the simplest case (FIG. 14A) a phenotype map derived from three parameters has three axes, one for the intra-sample distance measure for each of the parameters ($P_1$ and $P_2$) and one for the only available pair-wise inter-sample distance measure ($P_1$-$P_2$). Increasing the number of analysed parameters to three increases the complexity of the map to a small degree (FIG. 14B) yielding six axes, one for the intra-sample distance measure for each of the parameters ($P_1$, $P_2$ and $P_3$) and three for the pair-wise inter-sample distance measures ($P_1$-$P_2$, $P_1$-$P_3$ and $P_2$-$P_3$). Further increasing the number of analysed parameters increases the number of distance map axes as described previously where the number of axes M is related to the number of parameters P by Equation 4.

Whatever the number of parameters and the consequent level of complexity of the phenotype distance map, any such map be broken down into a number of simple components each representing a single pair wise comparison. Hence as shown in FIG. 14 a map derived from analysis of three parameters where M=6 (FIG. 14B) may be broken down in to a series of constituent elements $B_1$, $B_2$ and $B_3$. For any given phenotype map of dimension M the number of constituent elements is as defined by Equation 3.

Breaking down the phenotype map into components based on pair wise comparisons allows individual pairings to be given a phenotype change score (S) based on the intra-sample (D) and inter-sample distance (d) scores for the parameter pair:

$$S=d(D_{P1}+D_{P2}) \qquad \text{Equation (6)}$$

wherein the score is subject to a weighting based on the inter-sample distance calculated for the pairing, i.e. two parameters with a high inter-sample distance indicating a lack of correlation will produce a higher score than the same parameter values accompanied by a low inter-sample distance score.

Figure 15:
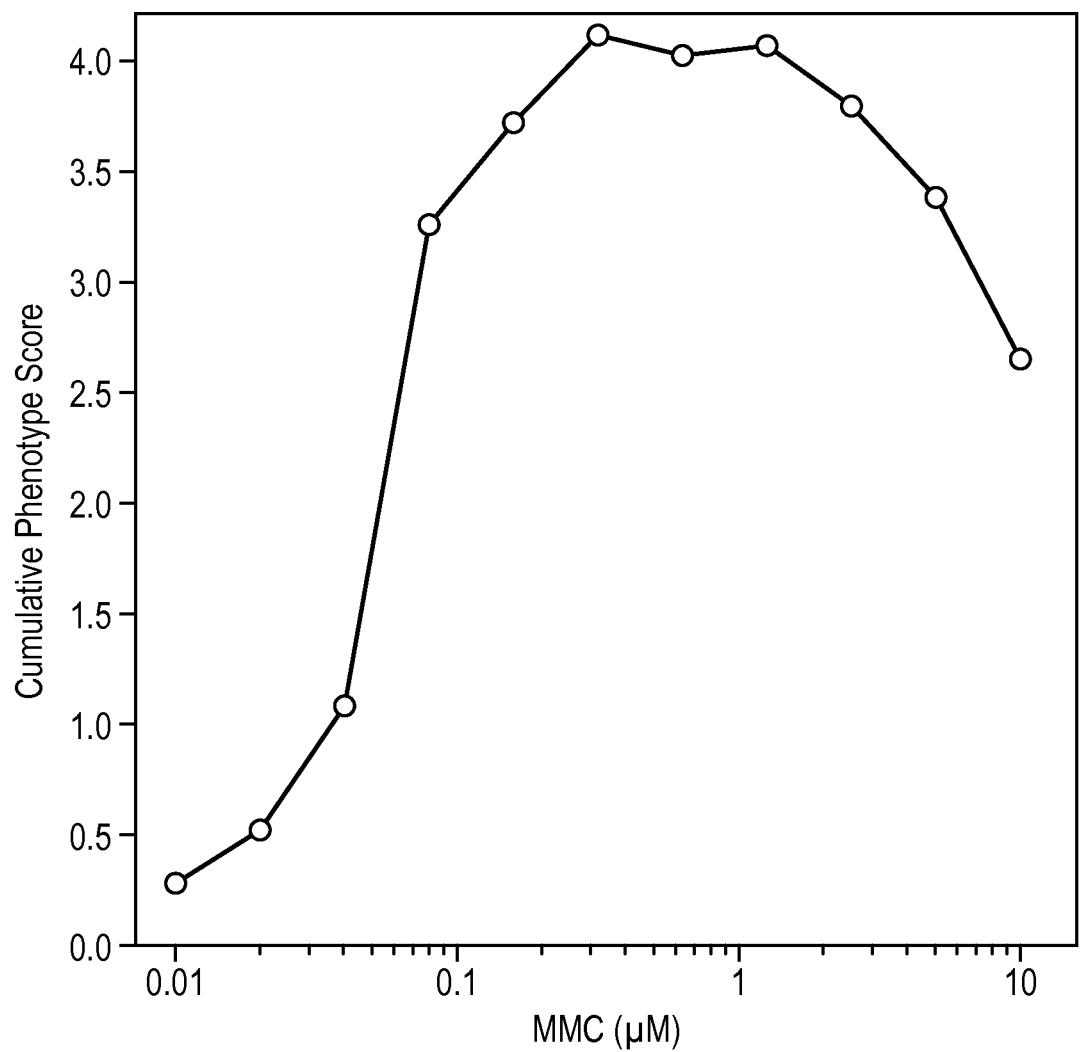
FIG. 15 shows phenotype scores derived from phenotype maps for cells treated with increasing concentrations of MMC in accordance with an aspect of the present invention.

For complex maps comprising greater that one component these scores can be calculated for each component and an overall phenotype change score calculated by summing the individual scores to yield a cumulative score taking account of all parameters measured in a HCS analysis. Cumulative phenotype scores for cells treated with a range of MMC concentrations and analysed for four nuclear morphology parameters are shown in FIG. 15.

It will be readily understood by those skilled in the art that further types of data comparison and cumulative scoring are possible based on the principles of combining intra-sample and inter-sample KS distance measures as described in the method according to aspects of the present invention. For example, the additional inclusion of base line inter-sample distance measures whereby KS distance measures obtained between different parameters in a control population in order to establish the degree of correlation between parameters allows further pair-wise comparisons and phenotype scoring to be undertaken.

Using the additional factor of control population inter-sample distance measures allows individual pairs of parameters to be given a phenotype change score (S) based on the intra-sample (D) distance scores for both parameters combined with inter-sample distance scores for both control ($d_c$) and treated ($d_t$) populations where the score takes into account the degree of correlation in the parameters under the two conditions:

$$S=(d_c+d_t)\times(D_{P1}+D_{P2}) \quad \text{Equation (7)}$$

This approach allows correlation changes across a range of conditions to be taken into account. For example, in a scenario where two parameters are not correlated in either control or test samples ($d_c$ and $d_t$ are both high) the resulting score will be maximised, conversely if the two parameters are correlated in both control and test samples ($d_c$ and $d_t$ are both low) the resulting score will be minimised.

Performing this operation for all parameter pairs and summing to produce a cumulative score provides a way to summarise data based on all HCS parameters measured.

The forgoing methods and other related embodiments of the present invention which encompass the use of both inter-sample and intra-sample population distribution distance measures allow very complex HCS datasets to be consolidated and summarised to measures which can be readily compared across large scale screening programs. The methods of various aspects and embodiments of the present invention are useful for evaluation of large scale drug, RNAi or other screening programs where the consolidation of multi-parameter data by such methods allow screening hits to be identified on the basis of combined phenotypic parameters and differential effects of treatment producing different phenotype classes, identified by different cumulative phenotype scores to be segregated.

By removing correlated parameters from a final analysis parameter set, various aspects and embodiments of the present invention can, for example, improve analysis efficiency by running small scale analysis, determining correlated parameters and then dropping the correlated parameters from an analysis parameter set that is subsequently used for a larger scale analysis.

Various aspects and embodiments of the present invention also, or alternatively, allow for modifying parameter values with respect to measured correlation, whilst retaining the modified parameters so that phenotypic scores comprise weighted aggregates of descriptive parameters such that correlated parameters do not overly influence the phenotypic score(s).

Whilst the present invention has been described in connection with various embodiments, those skilled in the art will be aware that many different embodiments and variations are possible. All such variations and embodiments are intended to fall within the scope of the present invention as defined by the appended claims.

What is claimed is:

1. A method for automated high-content screening (HCS) of a plurality of samples comprising cells and subjected to sample treatment conditions in an assay, wherein the plurality of samples comprise both samples subjected to a same treatment condition and samples subjected to different sample treatment conditions, the method comprising:
   processing data from each of two or more images of the plurality of samples to obtain a multi-parameter data set for each image;
   for samples subjected to the same sample treatment condition, obtaining inter-sample measurements based on distributions of different parameters in the same sample under the same sample treatment condition;
   for samples subjected to different sample treatment conditions, obtaining intra-sample measurements based on distributions of same parameter under the different sample treatment conditions;
   determining, based on both inter-sample and intra-sample measurements, correlated parameters in the respective multi-parameter data sets, wherein parameters from the multi-parameter data sets are graphically visualized in a phenotype map generated based on the inter-sample and intra-sample measurements and compared to determine the correlated parameters, and wherein correlation is to be determined using a Kolmogorov-Smirnov (KS) distance measurement analysis of parameters from the multi-parameter data sets;
   creating an analysis parameter set by removing at least one of the correlated parameters from the multi-parameter data sets to form the analysis parameter set;
   applying the analysis parameter set to identify one or more cellular phenotypes of the samples from the multi-parameter data sets; and
   providing an identification, in the plurality of samples, of one or more cells that undergo changes in cellular phenotypes.

2. The method of claim 1, further comprising identifying one or more phenotypes from a plurality of multi-parameter data sets and comparing respective phenotypes from the multi-parameter data sets to identify variations therebetween.

3. The method of claim 1, further comprising forming one or more respective analysis parameter sets for a plurality of multi-parameter data sets, and comparing the analysis parameter sets to determine whether or not a correlation relationship is maintained between the multi-parameter data sets.

4. The method of claim 1, wherein correlation is determined by the KS distance measurement analysis made between the phenotypes in a predetermined multi-parameter data analysis set.

5. The method of claim 4, wherein the KS distance measurement analysis includes a comparison of the frequency distribution of data within two data sets in the predetermined multi-parameter data analysis set.

6. The method of claim 1, wherein modifying correlated parameter values within the predetermined multi-parameter data analysis set comprises removing one of a pair of parameters whose correlation exceeds a predetermined threshold value from the analysis parameter set.

7. A tangible non-transient computer program storage product comprising machine instructions operable to configure a data processing apparatus to:
   process data from each of two or more images of a plurality of samples to obtain a multi-parameter data set for each image;
   for samples subjected to a same sample treatment condition, obtain inter-sample measurements based on distributions of different parameters in the same sample under the same sample treatment condition;
   for samples subjected to different sample treatment conditions, obtain intra-sample measurements based on distributions of same parameter under the different sample treatment conditions;
   determine, based on both inter-sample and intra-sample measurements, correlated parameters in the respective multi-parameter data sets, wherein parameters from the multi-parameter data sets are graphically visualized in a phenotype map generated based on the inter-sample and intra-sample measurements and compared to determine the correlated parameters, and wherein correlation is to be determined using a Kolmogorov-Smirnov (KS) distance measurement analysis of parameters from the multi-parameter data sets;

create an analysis parameter set by removing at least one of the correlated parameters from the multi-parameter data sets to form the analysis parameter set;

apply the analysis parameter set to identify one or more cellular phenotypes of the samples from the multi-parameter data sets; and provide an identification, in the plurality of samples, of one or more cells that undergo changes in cellular phenotypes.

8. A system for automated high-content screening (HCS) of a plurality of samples comprising cells and subjected to sample treatment conditions in an assay, wherein the plurality of samples comprise both samples subjected to a same treatment condition and samples subjected to different sample treatment conditions, the system comprising:

an imager for obtaining two or more images of the plurality of samples, each image represented by a respective multi-parameter data set; and an image processor that is operable to:

process data from each of the two or more images to obtain respective ones of the multi-parameter data sets;

for samples subjected to the same sample treatment condition, obtain inter-sample measurements based on distributions of different parameters in the same sample under the same sample treatment condition;

for samples subjected to different sample treatment conditions, obtain intra-sample measurements based on distributions of same parameter under the different sample treatment conditions;

determine, based on both inter-sample and intra-sample measurements, correlated parameters in the respective multi-parameter data sets, wherein parameters from the multi-parameter data sets are graphically visualized in a phenotype map generated based on the inter-sample and intra-sample measurements and compared to determine the correlated parameters, and wherein correlation is to be determined using a Kolmogorov-Smirnov (KS) distance measurement analysis of parameters from the multi-parameter data sets;

create an analysis parameter set by removing at least one of the correlated parameters from the multi-parameter data sets to form the analysis parameter set;

apply the analysis parameter set to identify one or more cellular phenotypes of the samples from the multi-parameter data sets; and provide an identification, in the plurality of samples, of one or more cells that undergo changes in cellular phenotypes.

9. The system of claim 8, wherein the image processor is further operable to identify one or more phenotypes from a plurality of multi-parameter data sets and compare respective phenotypes from the multi-parameter data sets to identify variations therebetween.

10. The system of claim 8, wherein the image processor is further operable to form two or more respective analysis parameter sets for a plurality of multi-parameter data sets, and compare the analysis parameter sets to determine whether or not a correlation relationship is maintained between the multi-parameter data sets.

11. The system of claim 8, wherein the image processor is further operable to determine correlation by using the KS distance measurement analysis made between the parameters in a predetermined multi-parameter data analysis set.

12. The system of claim 11, wherein the KS distance measurement analysis includes a comparison of the frequency distribution of data within two data sets in the predetermined multi-parameter data analysis set.

13. The system of claim 8, wherein the image processor is further operable to modify correlated parameter values within a predetermined multi-parameter data analysis set by removing one of a pair of parameters whose correlation exceeds a predetermined threshold value from the analysis parameter set.

14. The system of claim 8, wherein the two or more images comprise cellular images and the imager comprises a cellular imager.

15. The system of claim 14, wherein each multi-parameter data set includes one or more parameters of: nuclear area; length; diameter; perimeter; ellipticity; and weighted moment of inertia (WMOI), form, and distribution.

16. The system of claim 14, wherein the intra-sample measurements are used in weighting and prioritizing data produced from the inter-sample measurements to produce a single phenotype score measure summarizing a cumulative difference between two cellular populations across a range of measured parameters.

17. The system of claim 8, wherein the image processor is further configured to produce one or more phenotype maps graphically representing phenotypic signatures based on intra-sample measurements and inter-sample measurements.

18. The system of claim 17, wherein the inter-sample measurements and the intra-sample measurements comprise population comparator measures.

19. The system of claim 18, wherein the population comparator measures comprise Kolmogorov-Smirnov (KS) distance measurements.

20. The system of claim 8, wherein the intra-sample measurements are utilized to measure changes in the inter-sample measurements to provide phenotype characterization data.

21. The system of claim 8, wherein the sample is subjected to a drug treatment.

22. The system of claim 8, wherein the sample comprises a cellular population and the two or more images comprises a microscope image of the cellular population.

23. The system of claim 8, wherein identifying cells that undergo changes in cellular phenotypes comprises detecting changes in interrelationships of correlated parameters based on inter sample measurement.

24. The system of claim 8, the image processor is further operable to generate, based on a combination of inter-sample and intra-sample measurements, phenotype maps graphically representing phenotypic signatures.

* * * * *